(12) United States Patent
Leibler et al.

(10) Patent No.: US 10,286,101 B2
(45) Date of Patent: May 14, 2019

(54) METHODS FOR ADHERING TISSUE SURFACES AND MATERIALS AND BIOMEDICAL USES THEREOF

(71) Applicants: INSERM (INSTITUT NATIONAL DE LA SANTÉ ET DE LA RECHERCHE MÉDICALE), Paris (FR); UNIVERSITÉ PARIS DIDEROT—PARIS 7, Paris (FR); CENTRE NATIONAL DE LA RECHERCHE SCIENTIFIQUE (CNRS), Paris (FR); UNIVERSITÉ PARIS XIII PARIS-NORD, Villetaneuse (FR); ECOLE SUPERIEURE DE PHYSIQUE ET DE CHIMIE INDUSTRIELLES DE PARIS, Paris (FR); UNIVERSITÉ PIERRE ET MARIE CURIE (PARIS 6), Paris (FR)

(72) Inventors: Ludwik Leibler, Paris (FR); Anne Meddahipelle, Paris (FR); Didier Letourneur, Paris (FR); Alba Marcellan-Parisot, Paris (FR)

(73) Assignees: INSERM (Institut National de la Santé et de la Recherche Médicale), Paris (FR); Université Paris Diderot—Paris 7, Paris (FR); Centre National de la Recherche Scientifique (CNRS), Paris (FR); Université Paris XIII Paris-Nord, Villetaneuse (FR); École Supérieur de Physique et de Chimie Industrielles de Paris, Paris (FR)

( * ) Notice: Subject to any disclaimer, the term of this patent is extended or adjusted under 35 U.S.C. 154(b) by 61 days.

(21) Appl. No.: 15/102,541

(22) PCT Filed: Dec. 10, 2014

(86) PCT No.: PCT/EP2014/077122
§ 371 (c)(1),
(2) Date: Jun. 8, 2016

(87) PCT Pub. No.: WO2015/086640
PCT Pub. Date: Jun. 18, 2015

(65) Prior Publication Data
US 2016/0325010 A1    Nov. 10, 2016

(30) Foreign Application Priority Data

Dec. 10, 2013 (EP) .................... 13306692
Feb. 17, 2014 (EP) .................... 14305211

(51) Int. Cl.
*A61L 24/02* (2006.01)
*A61L 26/00* (2006.01)
(Continued)

(52) U.S. Cl.
CPC ......... *A61L 24/0015* (2013.01); *A61L 24/001* (2013.01); *A61L 24/0005* (2013.01);
(Continued)

(58) Field of Classification Search
CPC ...... A61L 24/00; A61L 24/02; A61L 24/0068; A61L 24/0089; A61L 26/0004
See application file for complete search history.

(56) References Cited

U.S. PATENT DOCUMENTS

| 4,477,607 | A | * | 10/1984 | Litke | ................... | A61B 5/1172 |
|---|---|---|---|---|---|---|
| | | | | | | 523/212 |
| 6,155,265 | A | * | 12/2000 | Hammerslag | ...... | A61B 17/0057 |
| | | | | | | 128/898 |

(Continued)

FOREIGN PATENT DOCUMENTS

| GB | 1261281 A * 1/1972 | ............. A61L 24/06 |
|---|---|---|
| WO | 03/026481 A2 4/2003 | |

(Continued)

OTHER PUBLICATIONS

Liu, Hui, et al. "Silica Nanoparticles as Adhesives for Biological Tissues? Re-Examining the Effect of Particles Size, Particle Shape, and the Unexpected Role of Base." Particle & Particle Systems Characterization 34.12 (2017): 1700286.*
Gryshchuk, Volodymyr, and Natalya Galagan. "Silica nanoparticles effects on blood coagulation proteins and platelets." Biochemistry research international 2016 (2016).*
Ilinskaya, Anna N., and Marina A. Dobrovolskaia. "Nanoparticles and the blood coagulation system. Part II: safety concerns." Nanomedicine 8.6 (2013): 969-981.*

(Continued)

*Primary Examiner* — Bethany P Barham
*Assistant Examiner* — Peter Anthopolos
(74) *Attorney, Agent, or Firm* — W & C IP

(57) ABSTRACT

The present invention relates to methods for adhering tissue surfaces and materials and biomedical uses thereof. In particular the present invention relates to a method for adhering a first tissue surface to a second tissue surface in a subject in need thereof, comprising the steps of adsorbing a layer of nanoparticles on at least one of the tissue surfaces, and approximating the surfaces for a time sufficient for allowing the surfaces to adhere to each other. The present invention also relates to a method for adhering a material to a biological tissue in a subject in need thereof, comprising the steps of adsorbing a layer of nanoparticles on the surface of the material and/or the biological tissue and approximating the material and the biological tissue for a time sufficient for allowing the material and the biological tissue to adhere to each other.

18 Claims, 12 Drawing Sheets

(51) Int. Cl.
*A61L 24/00* (2006.01)
*A61L 24/08* (2006.01)

(52) U.S. Cl.
CPC ............. *A61L 24/02* (2013.01); *A61L 24/08* (2013.01); *A61L 26/0004* (2013.01); *A61L 26/0023* (2013.01); *A61L 26/0057* (2013.01); *A61L 26/0061* (2013.01); *A61L 26/0066* (2013.01); *A61F 2210/0076* (2013.01); *A61F 2240/001* (2013.01); *A61F 2250/0009* (2013.01); *A61L 2400/02* (2013.01); *A61L 2400/12* (2013.01)

(56) References Cited

U.S. PATENT DOCUMENTS

| | | | | |
|---|---|---|---|---|
| 7,649,045 | B2* | 1/2010 | Karpowicz | A61L 15/18 524/492 |
| 7,670,623 | B2* | 3/2010 | Kotha | A61K 9/501 424/489 |
| 2006/0034935 | A1* | 2/2006 | Pronovost | A61K 9/7015 424/489 |
| 2006/0104970 | A1* | 5/2006 | Margel | A61K 31/00 424/94.64 |
| 2007/0154564 | A1* | 7/2007 | Stucky | A61K 33/00 424/603 |
| 2010/0092573 | A1* | 4/2010 | Lally | A61K 33/00 424/602 |
| 2011/0165221 | A1* | 7/2011 | Jung | A61F 13/00008 424/445 |
| 2014/0303261 | A1* | 10/2014 | Ramjit | A61L 24/06 514/770 |

FOREIGN PATENT DOCUMENTS

| | | |
|---|---|---|
| WO | 2004/045494 A2 | 6/2004 |
| WO | 2006/012541 A2 | 2/2006 |
| WO | 2015/036410 A1 | 3/2015 |

OTHER PUBLICATIONS

Tavano, Regina, et al. "Procoagulant properties of bare and highly PEGylated vinyl-modified silica nanoparticles." Nanomedicine 5.6 (2010): 881-896.*

Rose et al., "Nanoparticle solutions as adhesives for gels and biological tissues", Nature vol. 505, Jan. 16, 2014.

Meddahi-Pelle et al., "Organ Repair, Hemostasis, and in Vivo Bonding of Medical Devices by Aqueous Solutions of Nanoparticles", Angew. Chem. Int. Ed. 2014, 53, 6369-6373.

* cited by examiner

METHODS FOR ADHERING TISSUE SURFACES AND MATERIALS AND BIOMEDICAL USES THEREOF

FIELD OF THE INVENTION

The present invention relates to methods for adhering tissue surfaces and materials and biomedical uses thereof.

BACKGROUND OF THE INVENTION

A number of tissue adhesives have been used in various medical procedures and applications, including topical wound closure, supplementing or replacing surgical sutures or staples, adhesion of synthetic materials to biological tissues, and drug delivery. These substances are characterized by the ability to polymerize and, thus, form a solid precipitate from a stable liquid monomeric form, amenable to catheter or needle injection.

The most widely used tissue adhesives are generally unfit for use as hemostatic or internal fluid-stasis devices, for reasons generally related to mild toxicity and inability to be easily prepared and applied in the field. A good example of this is the cyanoacrylate family of topical skin adhesives, such as Dermabond™, Indermil™, Liquiband™ etc. The nature of cyanoacrylate's rapid activation when exposed to air renders cyanoacrylate-based products inappropriate for use in an active hemostatic field dressing and their inability to bind to wet surfaces renders them inappropriate for internal hemostatis or fluid-stasis usage.

Existing products that are intended for internal fluid-stasis usage also have significant problems. BioGlue™ (Cryolife Inc.) is a strong adhesive and sealant but contains albumin crosslinked by glutaraldehyde, a substance which is toxic and highly neurotoxic. Another sealant is CoSeal (Baxter), which is composed of polyethylene glycol (PEG). Though it is non-toxic, it has only weak adhesive strength, greatly limiting its applications. Gelatin has been used in a variety of wound dressings. Since gelatin gels have a relatively low melting point, they are not very stable at body temperature. Therefore, it is imperative to stabilize these gels by establishing cross-links between the protein chains. In practice, this is usually obtained by treating the gelatin with glutaraldehyde or formaldehyde. Thus, cross-linked gelatin may be fabricated into dry sponges which are useful for inducing hemostasis in bleeding wounds. Commercially available examples of such sponges include Spongostan (Ferrosan, Denmark), Gelfoam (Upjohn, USA), and Surgifoam (Ethicon. Somerville, N.J.). A major disadvantage of these sponges is that the cross-linking agent used (formaldehyde or glutaraldehyde) is toxic for cells.

Therefore, it highly desirable to provide improved adhesive methods that overcome one or more of the above-described disadvantages.

SUMMARY OF THE INVENTION

The present invention relates to methods for adhering tissue surfaces and materials and biomedical uses thereof. In particular the present invention is defined by the claims.

DETAILED DESCRIPTION OF THE INVENTION

Sutures are traumatic to soft connective tissues such as liver or lungs. Polymer tissue adhesives require complex in vivo control of polymerization or cross-linking reactions and currently suffer from being toxic, weak or inefficient within the wet conditions of the body. Herein, the inventors demonstrate using Stöber silica or iron oxide nanoparticles that nanobridging, adhesion by aqueous nanoparticle solutions, can be used in vivo in rats to achieve rapid and strong closure and healing of deep wounds in tissues as different as skin and liver. Nanoparticles were also used to fix polymer membranes to tissues even in the presence of blood flow such as occurring after liver resection, yielding permanent hemostasis within a minute. Furthermore, medical devices and tissue engineering constructs were secured to organs such as a beating heart. The simplicity, rapidity, and robustness of nanobridging bode well for translation to clinical applications, surgery and regenerative medicine.

The present invention relates to a method for adhering a first tissue surface to a second tissue surface in a subject in need thereof, comprising the steps of adsorbing a layer of nanoparticles on at least one of the tissue surfaces, and approximating the surfaces for a time sufficient for allowing the surfaces to adhere to each other.

The method of the invention may be carried out with any subject. The subject is preferably a mammal, more preferably a primate and more preferably still, a human. Subjects may be male or female and may be of any age, including prenatal (i.e., in utero), neonatal, infant, juvenile, adolescent, adult, and geriatric subjects.

In some embodiments, the method of the present invention is applied to at least one tissue surface selected from the group consisting of skin tissue, hair tissue, nail tissue, corneal tissue, tongue tissue, oral cavity tissue, esophageal tissue, anal tissue, urethral tissue, vaginal tissue, urinary epithelial tissue, salivary gland tissue, mammary gland tissue, lacrimal gland tissue, sweat gland tissue, prostate gland tissue, bulbourethral gland tissue, Bartholin's gland tissue, uterine tissue, respiratory and gastrointestinal tract goblet cell tissue, gastric mucosal tissue, gastric gland tissue, pancreatic tissue, spleen tissue, pulmonary tissue, pituitary gland tissue, thyroid gland tissue, parathyroid gland tissue, testicular tissue, ovarian tissue, respiratory gland tissue, gastrointestinal gland tissue, adrenal gland tissue, renal tissue, liver tissue, adipose tissue, duct cell tissue, gall bladder tissue, epidydimal tissue, vas deferens tissue, blood vessel tissue, lymph gland tissue, lymphatic duct tissue, synovial tissue, serosal tissue, squamous tissue, cochlear tissue, choroid plexus tissue, ependymal tissue, dural tissue, pia-arachnoid tissue, sclera tissue, retinal tissue, iris tissue, ciliary tissue, dental tissue, otic tissue, ligament tissue, tendon tissue, elastic cartilage tissue, fibrocartilage tissue, hyaline cartilage tissue, bone marrow tissue, intervertebral disc tissue, compact bone tissue, cancellous bone tissue, skeletal muscle tissue, cardiac muscle tissue, smooth muscle tissue, cardiac valve tissue, pericardial tissue, pleural tissue, peritoneal tissue, blood cell tissue, neuronal tissue, glial tissue, sensory transducer cell tissue, pain sensitive tissue, autonomic neuron tissue, peripheral nervous system tissue, cranial nerve tissue, ocular lens tissue, germ cell tissue, thymus tissue, placental tissue, fetal membrane tissue, umbilical tissue, stem cell tissue, mesodermal tissue, ectodermal tissue, endodermal tissue, autologous tissue, allograft tissue or a combination thereof.

The present invention also relates to a method for adhering a material to a biological tissue in a subject in need thereof, comprising the steps of adsorbing a layer of nanoparticles on the surface of the material and/or the biological tissue and approximating the material and the biological tissue for a time sufficient for allowing the material and the biological tissue to adhere to each other.

As used herein, the term "material" denotes any material that can be used to adhere to a tissue, for any purposes, including but not limiting to, research purposes, diagnostic purposes, and therapeutic purposes. Typically the material is a natural material or is an artificial material (i.e. a man-made material). The material can be less or more solid, less or more flexible, can have less or ability to swell . . . .

In some embodiments, the material is an artificial material. Typically the material is selected form the group consisting of membranes, scaffold materials, films, sheets, tapes, patches, meshes or medical devices.

In some embodiments, the material is biocompatible material. As used herein, the term "biocompatible" generally refers having the property or characteristic of not generating injury, toxicity or immunological reaction to living tissues. Accordingly, the material does not substantively provoke injury, toxicity or an immunological reaction, such as a foreign body reaction or inflammatory response (in particular excessive inflammatory response), upon implantation of the material in a subject.

In some embodiments, the material is biodegradable. The term "biodegradable" as used herein is defined to include both bioabsorbable and bioresorbable materials. In particular, by "biodegradable", it is meant that the materials decompose, or lose structural integrity under body conditions (e.g., enzymatic degradation or hydrolysis) or are broken down (physically or chemically) under physiologic conditions in the body such that the degradation products are excretable or absorbable by the body.

According to the invention, the outer surface of the material shall have the capability of adsorbing the nanoparticles of the invention. In particular, the at least one surface of the material, or a part thereof is polar. In some embodiments, the material is made of metal, glass or polymers.

Typically the material may be made from any biocompatible polymer. The biocompatible polymer may be synthetic or natural. The biocompatible polymer may be biodegradable, non-biodegradable or a combination of biodegradable and non-biodegradable.

Representative natural biodegradable polymers which may be used include but are not limited to polysaccharides, such as alginate, dextran, chitin, hyaluronic acid, cellulose, collagen, gelatin, fucans, glycosaminoglycans, and chemical derivatives thereof (substitutions and/or additions of chemical groups, for example, alkyl, alkylene, hydroxylations, oxidations, and other modifications routinely made by those skilled in the art); and proteins, such as albumin, casein, zein, silk, and copolymers and blends thereof, alone or in combination with synthetic polymers.

Synthetically modified natural polymers which may be used include but are not limited to cellulose derivatives, such as alkyl celluloses, hydroxyalkyl celluloses, cellulose ethers, cellulose esters, nitrocelluloses, and chitosan. Examples of suitable cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate, and cellulose sulfate sodium salt. These are collectively referred to herein as "celluloses."

Representative synthetic degradable polymers suitable for use include but are not limited to polyhydroxy acids prepared from lactone monomers, such as glycolide, lactide, caprolactone, ε-caprolactone, valerolactone, and δ-valerolactone, as well as pluronics, carbonates (e.g., trimethylene carbonate, tetramethylene carbonate, and the like); dioxanones (e.g., 1,4-dioxanone and p-dioxanone), 1, dioxepanones (e.g., 1,4-dioxepan-2-one and 1,5-dioxepan-2-one), and combinations thereof. Polymers formed therefrom include: polylactides; poly(lactic acid); polyglycolides; poly (glycolic acid); poly(trimethylene carbonate); poly(dioxanone); poly(hydroxybutyric acid); poly(hydroxyvaleric acid); poly(lactide-co-(s-caprolactone-)); poly(glycolide-co-(8-caprolactone)); polycarbonates; poly(pseudo amino acids); poly(amino acids); poly(hydroxyalkanoate)s; polyalkylene oxalates; polyoxaesters; polyanhydrides; polyortho esters; and copolymers, block copolymers, homopolymers, blends, and combinations thereof.

Some non-limiting examples of suitable non-bioabsorbable materials include but are not limited to polyolefins, such as polyethylene and polypropylene including atactic, isotactic, syndiotactic, and blends thereof; polyethylene glycols; polyethylene oxides; ultra high molecular weight polyethylene; copolymers of polyethylene and polypropylene; polyisobutylene and ethylene-alpha olefin copolymers; fluorinated polyolefins, such as fluoroethylenes, fluoropropylenes, fluoroPEGSs, and polytetrafluoroethylene; polyamides, such as nylon and polycaprolactam; polyamines; polyimines; polyesters, such as polyethylene terephthalate and polybutylene terephthalate; aliphatic polyesters; polyethers; polyether-esters, such as polybutester; polytetramethylene ether glycol; 1,4-butanediol; polyurethanes; acrylic polymers and copolymers; modacrylics; vinyl halide polymers and copolymers, such as polyvinyl chloride; polyvinyl alcohols; polyvinyl ethers, such as polyvinyl methyl ether; polyvinylidene halides, such as polyvmylidene fluoride and polyvinylidene chloride; polyacrylonitrile; polyaryletherketones; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; alkyd resins; polycarbonates; polyoxymethylenes; polyphosphazine; polyimides; epoxy resins; aramids, rayon; rayon-triacetate; spandex; silicones; and combinations thereof.

In some embodiments, the material comprises a woven or non woven fabric used as biomedical prostheses and scaffolds for tissue engineering. They can be biodegradable or not in nature and are obtained by numerous manufactured methods including electrospinning to have small pore size, high porosity and high surface area.

In some embodiment, the material is a mesh, in particular a surgical mesh. As used herein, the term "mesh" is intended to include any element having an openwork fabric or structure, and may include but is not limited to, an interconnected network of wire-like segments, a sheet of material having numerous apertures and/or portions of material removed, or the like. As used herein the term "surgical mesh" is used to a mesh suitable for use in surgical procedures, such as, for example, meshes that do not require suturing to the abdominal wall. Surgical meshes, which are used to reinforce weakened areas of abdominal, pelvic, or thoracic tissues, or to replace a portion of internal structural soft tissue that has neither been damaged nor removed surgically, can also be made to have anti-adhesion properties. Surgical mesh drug eluting delivery devices can include one or more therapeutic agents provided with a drug eluting mesh wrap implant placed adjacent to medical devices and internal tissue as described therein. The meshes are available in various single layer, multi-layer, and 3-dimensional configurations made without bioabsorbable adhesion coatings and films. The meshes are most often constructed of synthetic non-absorbable polymer materials, such as polyethylene, polytetrafluoroethylene, and polypropylene, and can include a carrier having a therapeutic agent attached thereto, incorporated within, or coated thereon. Typically four different material groups have become available for hernia repair and abdominal wall reconstruction: PP, PTFE, ePTFE and Polyester (POL) (Yilmaz Bilsel, Ilker Abci The search for ideal hernia repair; mesh materials and types International Journal of Surgery 10 (2012) 317e321). PP is a hydrophobic polymer of carbon atoms with alternating methyl moieties. This material is flexible, strong, easily cut, readily integrated by surrounding tissues and resists infection. The monofilament nature provides large pores facilitating fibrovascular ingrowth, infection resistance and improved compliance. PP remains the most popular material in mesh hernia repair. PTFE is a chemically inert synthetic fluoropolymer which has a high negative charge, therefore water and oils do not adhere to it. This material does not incorporate into human tissue and becomes encapsulated. Poor tissue incorporation increases hernia recurrence and an infected PTFE mesh must be explanted. PTFE is micro porous, which allows bacteria passage but prevents macrophage passage; therefore the body cannot clear the infection. 8 and 9 PTFE was expanded to be improved, and it became a uniform, fibrous and micro porous structure with improved strength called ePTFE. Although it is not incorporated into tissue and has a high incidence of seroma formation, ePTFE remains inert and produces little inflammatory effects, which allows it to be placed directly on viscera. POL is a carbon polymer of terephthalic acid and can be fashioned into strong fibers suitable to be woven into a prosthetic mesh. It is a hydrophilic material and is degraded by hydrolysis. The mesh structure for this surgical application serves as a drug eluting delivery apparatus for local therapeutic delivery within the body. Affixing the carrier and or coating directly onto the surgical mesh makes it easier to handle the device without the drawbacks of film, namely tearing, folding, and rapid dissolving when contacting body fluids, and the lack of fixation or anchoring means. Non-absorbable mesh structures generally provide more handling strength and directional placement control during installation than bio-absorbable or bio-dissolvable polymer films.

In some embodiments, the material is an implant. Regular improvements have been made to facilitate the use of implants. These include: preformed or precut implants adapted to different techniques (4D Dome®; Ultrapro Plug®, Perfix Plug®) for the plug techniques; different pre-cut prostheses to allow the passage of the spermatic cord (Lichtenstein technique); meshes that assume the anatomical contours of the inguinal region for the pre-peritoneal technique (ex Swing Mesh 4A®, 3D Max®). In particular, the implant is designed to facilitate its implantation. Implants furnished with either an auto-adhesive cover (example: Swing Contact®, Adhesix®, Progrip®) or with thermo-inducted staples (example: Endorollfix®); Three-dimensional implants theoretically limiting the possibility of migration (example: UHS®, Ultrapro®, 3D Patch®, PHS®); Implants adapted to laparoscopic maneuvering, for example, pre-rolled to facilitate the passage in the trocar (example: Endoroll®), or with pre-inserted cardinal point sutures (example: Parietex®) may be suitable.

In some embodiments, the material is a bioprosthesis. The bioprosthesis used in abdominal wall surgery derive from animal (xenogeneic prostheses from porcine (dermis or intestinal mucosa) or bovine (pericardium) origin, reticulated or not) or human (allogenic) tissues. They are constituted by type I, III or IV collagen matrixes as well as sterile acellular elastin produced by decellularization, sterilization and viral inactivation, in order to enhance integration and cellular colonization of the prosthesis by the host tissues. Commercial examples include but are not limited to Tutopatch®, SIS®, Tissue Science® process, Surgiguard®, Strattice®, CollaMend®, Permacol®, Surgisis®, XenMatrix®, Veritas® (non-reticulated bovine pericardial bioprosthesis), Protexa (porcine dermis), Alloderm®, Flex HD® Acellular Hydrated Dermis and AlloMaxTM(formerly NeoformTM) (acellular collagen matrix derived from human dermis.

In some embodiments, the material is an orthopedic implant. Typically, orthopedic implant include but are not limited to prosthetic knees, hips, shoulders, fingers, elbows, wrists, ankles, fingers and spinal elements.

In particular, the material is a wound covering material, a wound prosthetic material, a wound curing material, a post-operative adhesion-preventing material or haemostatic wound dressing. In particular the material is an implantable material that will provide a therapeutically benefit to the subject. In particular, the material is a multi-layer structure.

In some embodiments, the material is a membrane. In particular, the thickness of the membrane can vary depending upon application but will typically range from about 0.5 mm to about 8 mm, with a possible range between about 2 mm and about 5 mm, and a thickness of about 3 mm being one possibility. In some embodiments, the membrane may be made of any material but the membrane is typically a collagen fiber membrane.

In some embodiments, the material is a small intestine submucosa (SIS) material. SIS is indeed used in wound care treatment, particularly the application of layers of SIS directly upon an open wound that has been debrided and cleaned. SIS has been described as a natural acellular biomaterial used to repair, support, and stabilize a wide variety of anatomical defects and traumatic injuries. The SIS material is a tissue engineered collagen matrix derived from porcine small intestinal submucosa that models the qualities of its host when implanted in human soft tissues. Further, it is taught that the SIS material provides a natural scaffold-like matrix with a three-dimensional structure and biochemical composition that attracts host cells and supports tissue remodeling.

In some embodiments, the material is a scaffold, in particular a hydrogel scaffold. The method of the present invention is indeed particularly suitable in tissue engineering. Tissue engineering is generally defined as the creation of tissue or organ equivalents by seeding of cells onto or into a scaffold suitable for implantation. The scaffolds must be biocompatible and cells must be able to attach and proliferate on the scaffolds in order for them to form tissue or organ equivalents. These scaffolds are therefore considered as substrates for cell growth either in vitro or in vivo. The attributes of an ideal biocompatible scaffold includes the ability to support cell growth either in vitro or in vivo, the ability to support the growth of a wide variety of cell types or lineages, the ability to be endowed with varying degrees of flexibility or rigidity required, the ability to have varying degrees of biodegradability, the ability to be introduced into the intended site in vivo without provoking secondary damage, and the ability to serve as a vehicle or reservoir for delivery of drugs or bioactive substances to the desired site of action. Hydrogels represent an appealing scaffold material because they are structurally similar to the extracellular matrix of many tissues, can often be processed under relatively mild conditions, and may be delivered in a minimally invasive manner. Consequently, hydrogels, a class of highly hydrated polymer materials (water content higher than 30% by weight), are utilized as scaffold materials for drug and growth factor delivery, engineering tissue replacements, and a variety of other applications.

Typically variety of synthetic and naturally derived materials may be used to form hydrogels for tissue engineering scaffolds. Synthetic materials include poly(ethylene oxide) (PEO), poly(vinyl alcohol) (PVA), poly(acrylic acid) (PAA), poly(propylene fumarate-co-ethylene glycol) (P(PF-co-EG)), polypeptides, poly(hydroxyethyl methacrylate) (PHEMA), poly(2-acrylamido-2-methylpropanesulfonic acid) (PAMPS), poly(acrylamide) (PAAm), poly(ethyleneoxide) (PEG), poly(N-isopropylacrylamide) (PNIPAM), cyclodextrin-based polyrotaxanes gels (CD-PRs), protein-grafted hydrogels, peptide-grafted hydrogels, DNA-grafted polyacrylamide, Terra-amine-terminated PEG (TAPEG), Tetra-NHS-glutarate-terminated PEG (TNPEG), Tetrahydroxyl-terminated PEG (THPEG), poly(dimethylacrylamide-co-acrylamide), poly(ethylene oxide-stat-propylene oxide) (sPEGPPG), poly(methyl methacrylate) and poly(methacrylic acid) triblock copolymers and double networks (DN) or semi-interpenetrating networks (IPN) such as photopolymerized PEG-diacrylate (PEG-DA), PEG and Photocrosslinkable 4-azidobenzoic acid-modified chitosan (Az-C), IPN of gelatin and dextran bifunctionalized with methacrylate (MA) and aldehyde (AD) (Dex-MA-AD), poly(ethylene glycol)/poly(acrylic acid) (PEG/PAAc), poly(ether-urethane)/poly(methyl-methacrylate) (PEU/PMMA), agarose/poly(ethylene glycol) diacrylate, modified hyaluronan/poly(N,N'-dimethylacrylamide) (PHA/PDMAAm), jellyfish/polyacrylamide (JF/PAAm), poly(vinyl alcohol) PVA/PEG, Poly(ethylene glycol) (PEG)/polydimethylsiloxane (PDMS) (PEG/PDMS), poly(acrylic acid)/poly(vinylalcohol), poly(3,4-ethylenedioxythiphene) (PEDOT)/PAMPS/PAAm, poly(ethylene oxide-propylene oxide) (sPEOPO).

Representative naturally derived polymers include agarose, alginate, chitosan, collagen, fibrin, gelatins, and hyaluronic acid (HA), dextran, chitosan, carrageenans. In particular any type of polysaccharide can be used. For example, suitable polysaccharides include, but are not limited to, dextran, agar, alginic acid, hyaluronic acid, inulin, pullulan, heparin, fucoidan, scleroglucan, curdlan, starch, cellulose and mixtures thereof. Monosaccharides that may be used to produce the desired polysaccharide include but are not limited to ribose, glucose, mannose, galactose, fructose, sorbose, sorbitol, mannitol, iditol, dulcitol and mixtures thereof. Many of these compounds are available commercially from companies such as Sigma-Aldrich (St. Louis, Mich., US). The preferred weight-average molecular weight for the polysaccharide is from about 10,000 Daltons to about 2,000,000 Daltons, more preferably from about 10,000 Daltons to about 500,000 Daltons, most preferably from about 10,000 Daltons to about 200,000 Daltons.

In some embodiments, the porous material (e.g. hydrogel) is prepared according to the method described in WO2009047346A1 or according to the method described in WO2009047347A1.

In some embodiments, the material (e.g. hydrogel) is porous. Typically, the average pore size of the material (e.g. hydrogel) is from about 100 nm to about 500 μm. The density of the pores is from about 4% to about 25%.

In some embodiments, biologically active agents may be incorporated in the material (e.g. hydrogel). Active agents amenable include growth factors, such as transforming growth factors (TGFs), fibroblast growth factors (FGFs), platelet derived growth factors (PDGFs), epidermal growth factors (EGFs), connective tissue activated peptides (CTAPs), osteogenic factors, and biologically active analogs, fragments, and derivatives of such growth factors. Members of the transforming growth factor (TGF) supergene family, which are multifunctional regulatory proteins, are particularly suitable. Members of the TGF supergene family include the beta transforming growth factors (for example, TGF-β1, TGF-β2, TGF-β3); bone morphogenetic proteins (for example, BMP-1, BMP-2, BMP-3, BMP-4, BMP-5, BMP-6, BMP-7, BMP-8, BMP-9); heparin-binding growth factors (for example, fibroblast growth factor (FGF), epidermal growth factor (EGF), platelet-derived growth factor (PDGF), insulin-like growth factor (IGF)); Inhibins (for example, Inhibin A, Inhibin B); growth differentiating factors (for example, GDF-1); and Activins (for example, Activin A, Activin B, Activin AB).

In addition to the biological active agents discussed above, a large number of pharmaceutical agents are known in the art and are amenable for use in the compositions of the invention. The term "pharmaceutical agent" includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

Non-limiting examples of broad categories of useful pharmaceutical agents include the following therapeutic categories: anabolic agents, antacids, anti-asthmatic agents, anti-cholesterolemic and anti-lipid agents, anti-coagulants, anti-convulsants, anti-diarrheals, anti-emetics, anti-infective agents, anti-inflammatory agents, anti-manic agents, anti-nauseants, anti-neoplastic agents, anti-obesity agents, anti-pyretic and analgesic agents, anti-spasmodic agents, anti-thrombotic agents, anti-uricemic agents, anti-anginal agents, antihistamines, anti-tussives, appetite suppressants, biologicals, cerebral dilators, coronary dilators, decongestants, diuretics, diagnostic agents, erythropoietic agents, expectorants, gastrointestinal sedatives, hyperglycemic agents, hypnotics, hypoglycemic agents, ion exchange resins, laxatives, mineral supplements, mucolytic agents, neuromuscular drugs, peripheral vasodilators, psychotropics, sedatives, stimulants, thyroid and anti-thyroid agents, uterine relaxants, vitamins, and prodrugs.

More specifically, non-limiting examples of useful pharmaceutical agents include the following therapeutic categories: analgesics, such as nonsteroidal anti-inflammatory drugs, opiate agonists and salicylates; antihistamines, such as H1-blockers and H2-blockers; anti-infective agents, such as anthelmintics, antianaerobics, antibiotics, aminoglycoside antibiotics, antifungal antibiotics, cephalosporin antibiotics, macrolide antibiotics, miscellaneous beta-lactam antibiotics, penicillin antibiotics, quinolone antibiotics, sulfonamide antibiotics, tetracycline antibiotics, antimycobacterials, antituberculosis antimycobacterials, antiprotozoals, antimalarial antiprotozoals, antiviral agents, anti-retroviral agents, scabicides, and urinary anti-infectives; antineoplastic agents, such as alkylating agents, nitrogen mustard alkylating agents, nitrosourea alkylating agents, antimetabolites, purine analog antimetabolites, pyrimidine analog antimetabolites, hormonal antineoplastics, natural antineoplastics, antibiotic natural antineoplastics, and *vinca* alkaloid natural antineoplastics; autonomic agents, such as anticholinergics, antimuscarinic anticholinergics, ergot alkaloids, parasympathomimetics, cholinergic agonist parasympathomimetics, cholinesterase inhibitor para-sympathomimetics, sympatholytics, alpha-blocker sympatholytics, beta-blocker sympatholytics, sympathomimetics, adrenergic agonist sympathomimetics; cardiovascular agents, such as antianginals, beta-blocker antianginals, calcium-channel blocker antianginals, nitrate antianginals, antiarrhythmics, cardiac glycoside antiarrhythmics, class I antiarrhythmics, class II antiarrhythmics, class III antiarrhythmics, class IV antiarrhythmics, antihypertensive agents, alpha-blocker antihypertensives, angiotensin-converting enzyme inhibitor (ACE inhibitor) antihypertensives, beta-blocker antihypertensives, calcium-channel blocker antihypertensives, central-acting adrenergic antihypertensives, diuretic antihypertensive agents, peripheral vasodilator antihypertensives, antilipemics, bile acid sequestrant antilipemics, HMG-CoA reductase inhibitor antilipemics, inotropes, cardiac glycoside inotropes, and thrombolytic agents; dermatological agents, such as antihistamines, anti-inflammatory agents, corticosteroid anti-inflammatory agents, antipruritics/local anesthetics, topical anti-infectives, antifungal topical anti-infectives, antiviral topical anti-infectives, and topical antineoplastics; electrolytic and renal agents, such as acidifying agents, alkalinizing agents, diuretics, carbonic anhydrase inhibitor diuretics, loop diuretics, osmotic diuretics, potassium-sparing diuretics, thiazide diuretics, electrolyte replacements, and uricosuric agents; enzymes, such as pancreatic enzymes and thrombolytic enzymes; gastrointestinal agents, such as antidiarrheals, antiemetics, gastrointestinal anti-inflammatory agents, salicylate gastrointestinal anti-inflammatory agents, antacid anti-ulcer agents, gastric acid-pump inhibitor anti-ulcer agents, gastric mucosal anti-ulcer agents, H2-blocker anti-ulcer agents, cholelitholytic agents, digestants, emetics, laxatives and stool softeners, and prokinetic agents; general anesthetics, such as inhalation anesthetics, halogenated inhalation anesthetics, intravenous anesthetics, barbiturate intravenous anesthetics, benzodiazepine intravenous anesthetics, and opiate agonist intravenous anesthetics; hematological agents, such as antianemia agents, hematopoietic antianemia agents, coagulation agents, anticoagulants, hemostatic coagulation agents, platelet inhibitor coagulation agents, thrombolytic enzyme coagulation agents, and plasma volume expanders; hormones and hormone modifiers, such as abortifacients, adrenal agents, corticosteroid adrenal agents, androgens, antiandrogens, antidiabetic agents, sulfonylurea antidiabetic agents, antihypoglycemic agents, oral contraceptives, progestin contraceptives, estrogens, fertility agents, oxytocics, parathyroid agents, pituitary hormones, progestins, antithyroid agents, thyroid hormones, and tocolytics; immunobiologic agents, such as immunoglobulins, immunosuppressives, toxoids, and vaccines; local anesthetics, such as amide local anesthetics and ester local anesthetics; musculoskeletal agents, such as anti-gout anti-inflammatory agents, corticosteroid anti-inflammatory agents, gold compound anti-inflammatory agents, immuno-suppressive anti-inflammatory agents, nonsteroidal anti-inflammatory drugs (NSAIDs), salicylate anti-inflammatory agents, skeletal muscle relaxants, neuromuscular blocker skeletal muscle relaxants, and reverse neuromuscular blocker skeletal muscle relaxants; neurological agents, such as anticonvulsants, barbiturate anticonvulsants, benzodiazepine anticonvulsants, anti-migraine agents, anti-parkinsonian agents, anti-vertigo agents, opiate agonists, and opiate antagonists; ophthalmic agents, such as anti-glaucoma agents, beta-blocker anti-glaucoma agents, miotic anti-glaucoma agents, mydriatics, adrenergic agonist mydriatics, antimuscarinic mydriatics, ophthalmic anesthetics, ophthalmic anti-infectives, ophthalmic aminoglycoside anti-infectives, ophthalmic macrolide anti-infectives, ophthalmic quinolone anti-infectives, ophthalmic sulfonamide anti-infectives, ophthalmic tetracycline anti-infectives, ophthalmic anti-inflammatory agents, ophthalmic corticosteroid anti-inflammatory agents, and ophthalmic nonsteroidal anti-inflammatory drugs (NSAIDs); psychotropic agents, such as antidepressants, heterocyclic antidepressants, monoamine oxidase inhibitors (MAOIs), selective serotonin re-uptake inhibitors (SSRIs), tricyclic antidepressants, antimanics, antipsychotics, phenothiazine antipsychotics, anxiolytics, sedatives, and hypnotics, barbiturate sedatives and hypnotics, benzodiazepine anxiolytics, sedatives, and hypnotics, and psychostimulants; respiratory agents, such as antitussives, bronchodilators, adrenergic agonist bronchodilators, antimuscarinic bronchodilators, expectorants, mucolytic agents, respiratory anti-inflammatory agents, and respiratory corticosteroid anti-inflammatory agents; toxicology agents, such as antidotes, heavy metal antagonists/chelating agents, substance abuse agents, deterrent substance abuse agents, and withdrawal substance abuse agents; minerals; and vitamins, such as vitamin A, vitamin B, vitamin C, vitamin D, vitamin E, and vitamin K.

Further specific examples of useful pharmaceutical agents from the above categories include: (a) anti-neoplastics such as androgen inhibitors, antimetabolites, cytotoxic agents, and immunomodulators; (b) anti-tussives such as dextromethorphan, dextromethorphan hydrobromide, noscapine, carbetapentane citrate, and chlophedianol hydrochloride; (c) antihistamines such as chlorpheniramine maleate, phenindamine tartrate, pyrilamine maleate, doxylamine succinate, and phenyltoloxamine citrate; (d) decongestants such as phenylephrine hydrochloride, phenylpropanolamine hydrochloride, pseudoephedrine hydrochloride, and ephedrine; (e) various alkaloids such as codeine phosphate, codeine sulfate and morphine; (f) mineral supplements such as potassium chloride, zinc chloride, calcium carbonates, magnesium oxide, and other alkali metal and alkaline earth metal salts; (g) ion exchange resins such as cholestryramine; (h) anti-arrhythmics such as N-acetylprocainamide; (i) antipyretics and analgesics such as acetaminophen, aspirin and ibuprofen; (j) appetite suppressants such as phenyl-propanolamine hydrochloride or caffeine; (k) expectorants such as guaifenesin; (l) antacids such as aluminum hydroxide and magnesium hydroxide; (m) biologicals such as peptides, polypeptides, proteins and amino acids, hormones, interferons or cytokines, and other bioactive peptidic compounds, such as interleukins 1-18 including mutants and analogues, RNase, DNase, luteinizing hormone releasing hormone (LHRH) and analogues, gonadotropin releasing hormone (GnRH), transforming growth factor-.beta. (TGF-beta), fibroblast growth factor (FGF), tumor necrosis factor-alpha & beta (TNF-alpha & beta), nerve growth factor (NGF), growth hormone releasing factor (GHRF), epidermal growth factor (EGF), fibroblast growth factor homologous factor (FGFHF), hepatocyte growth factor (HGF), insulin growth factor (IGF), invasion inhibiting factor-2 (IIF-2), bone morphogenetic proteins 1-7 (BMP 1-7), somatostatin, thymosin-alpha-1, gamma-globulin, superoxide dismutase (SOD), complement factors, hGH, tPA, calcitonin, ANF, EPO and insulin; and (n) anti-infective agents such as antifungals, anti-virals, antiseptics and antibiotics.

The biologically active substances are used in amounts that are therapeutically effective. While the effective amount of a biologically active substance will depend on the particular material being used, amounts of the biologically active substance from about 1% to about 65% may be desirable. Lesser amounts may be used to achieve efficacious levels of treatment for certain biologically active substances.

In some embodiments, the material (e.g. hydrogel) comprises an amount of a radiosensitizer. Radiosensitizers are drugs that make cancer cells more sensitive to the effects of radiation therapy. Non-limiting examples of metal radiosensitizers that could be used in accordance with the present invention include metals, preferably inert metals such as platinum, gold, iridium, osmium, palladium, radium, zinc, chromium, copper, silver, cobalt, nickel and ruthenium. The greater the atomic number, the better is the interaction with radiation. Other useful metals, although less preferred because of their small atomic number, include iron. Other examples of radio sensitizers include but are not limited to metoclopramide, sensamide or neusensamide (manufactured by Oxigene); profiromycin (made by Vion); RSR13 (made by Allos); Thymitaq (made by Agouron), etanidazole or lobenguane (manufactured by Nycomed); gadolinium texaphrin (made by Pharmacyclics); BuDR/Broxine (made by NeoPharm); IPdR (made by Sparta); CR2412 (made by Cell Therapeutic); L1X (made by Terrapin); or the like.

Accordingly, materials (e.g. hydrogel) comprising amount of radiosensitizers are particularly suitable for the treatment of cancer by radiotherapy. Once the material (e.g. hydrogel) is adhered to the cancer tissue, radiotherapy can be applied. Typically, the cancer is selected from the group consisting of breast cancer, prostate cancer, lymphoma, skin cancer, pancreatic cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, chronic granulocytic leukemia, acute granulocytic leukemia, acute myelogenous leukemia, chronic myelogenous leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, and retinoblastoma.

In some embodiments, the porous materials (e.g. hydrogels) are loaded with a plurality of cells. A difference in porosity may indeed facilitate migration of different cell types to the appropriate regions of the material (e.g. hydrogel). In another embodiment, a difference in porosity may facilitate development of appropriate cell-to-cell connections among the cell types comprising the material (e.g. hydrogel), required for appropriate structuring of the developing/repairing/regenerating tissue. For example, cell processes extension may be accommodated more appropriately via the varied porosity of the scaffolding material. Therefore, the material (e.g. hydrogel) may comprise cells of any tissue.

Typically, the cells are seeded on the material (e.g. hydrogel). Alternatively, the materials (e.g. hydrogels) are submerged in a culture solution comprising the desired cells for an amount of time sufficient to enable penetration of the cells throughout the material (e.g. hydrogel). In particular, the material (e.g. hydrogel) is capable of supporting the viability and the growth of the seeded cells in culture over long periods of time without inducing differentiation. More particularly, the material (e.g. hydrogel) of the invention can provide an environment for unstimulated cell growth (without activation by growth stimulants)

In some embodiments, the cells are pluripotent stem cells or progenitor cells. Pluripotent stem cells have the potential to differentiate into endoderm, mesoderm, and ectoderm. As used herein, "pluripotent" includes pluripotent stem cells from all sources, including embryonic stem cells (ESCs), modified adult stem or somatic cells (ASCs), that is, induced pluripotent stem cells (iPSC), and very small embryonic-like stem cells (VSELs). Embryonic pluripotent stem cells traditionally arise from the blastocyst stage of embryonic development and have the ability to develop into all types of fetal and adult cells except perhaps for placenta. Pluripotent stem cells have also been artificially generated (i.e., induced pluripotent stem cells (iPSC)) from other sources, such as placenta or from genetic manipulation of adult stem cells (ASC) or even adult somatic cells. ASC are located in tissues throughout the body and function as a reservoir to replace damaged or aging cells. ASC are generally restricted in their differentiation to cell lineages of the organ system from which they originate (i.e., "multipotent" stem cells), although recent research suggests that adult tissues, such as bone marrow, may harbor dormant pluripotent stem cells referred to as "very small embryonic-like stem cells" or "VSELs."

Typically, various animal ESC lines, such as, for example, NIH approved cell line WA09 human ESCs can be obtained commercially from WiCell Research Institute, Madison, Wis. Human ESC line Ceco-14, utilized herein, can be obtained commercially from Cecolfes, Bogota, Colombia. Of course, other embryonic stem cell lines may be used, if desired.

Typically, adult stem cells can be isolated from mammalian tissue, including from any adult organ, umbilical cord blood, or placenta. The adult stem cells are multipotent, but they may be manipulated to provide pluripotent stem cells (iPSC.) using conventional techniques.

In some embodiments, the stem cells can be derived from mammals, such as but not limited to rodents, pigs, cats, dogs, and primates, including humans.

In some embodiments, the pluripotent stem cells useful herein are nonviable. Advantageously, nonviable stem cells do not form teratomas. Typically, the stem cells may be made nonviable with irradiation, phototherapy, chemical treatment, and/or lyophilization. The selection of the method of making pluripotent stem cells nonviable is not particularly limited, but it is preferred that the method used is effective to retain the intracellular contents of the stem cells.

In some embodiments, the material (e.g. hydrogel) is seeded with cells selected from the group consisting of chondrocytes; fibrochondrocytes; osteocytes; osteoblasts; osteoclasts; synoviocytes; bone marrow cells; mesenchymal cells; muscle cells; stromal cells; stem cells; embryonic stem cells; precursor cells derived from adipose tissue; peripheral blood progenitor cells; stem cells isolated from adult tissue; genetically transformed cells; a combination of chondrocytes and other cells; a combination of osteocytes and other cells; a combination of synoviocytes and other cells; a combination of bone marrow cells and other cells; a combination of mesenchymal cells and other cells; a combination of stromal cells and other cells; a combination of stem cells and other cells; a combination of embryonic stem cells and other cells; a combination of progenitor cells isolated from adult tissue and other cells; a combination of peripheral blood progenitor cells and other cells; a combination of stem cells isolated from adult tissue and other cells; and a combination of genetically transformed cells and other cells.

In some embodiments the cells may be genetically engineered to express a desired molecule, such as for example heparin binding growth factor (HBGF), transforming growth factor alpha or beta (TGF beta.), alpha fibroblastic growth factor (FGF), epidermal growth factor (TGF), vascular endothelium growth factor (VEGF) and SDF-1, some of which are also angiogenic factors. In another embodiment expressed factors include hormones such as insulin, glucagon, and estrogen. In another embodiment factors such as nerve growth factor (NGF) or muscle morphogenic factor (MMF), or in another embodiment, TNF alpha/beta are expressed.

In some embodiments, the hydrogels according to the invention are suitable to prepare vascular substitutes to replace compromised arteries as described for example, in Chaouat et al. (Chaouat M, Le Visage C, Autissier A, Chaubet F, Letourneur D. The evaluation of a small-diameter polysaccharide-based arterial graft in rats. Biomaterials. 2006 November; 27(32):5546-53). Such substitutes may be prepared according to the methods of the invention by using a mould. Such substitutes may then comprise a population of cells to reconstruct in vitro or in vivo a vessel. In another embodiment the cells may include but are not limited to Mesenchymal Stem Cells (MSC), Endothelial Progenitor cells (EPCs), endothelial cells, fibroblastic cells and smooth muscle cells.

In some embodiments, the materials (e.g. hydrogel) of the invention are suitable to prepare cartilage implants. In such a way, the scaffolds of the invention may be loaded with chondrocytes, osteocytes; osteoblasts; osteoclasts; vascular cells or mixtures thereof, and then be fixing to the cartilage to be repaired by the nanoparticles of the present invention.

The site of implantation of the material (e.g. hydrogel) is dependent on the diseased/injured tissue that requires treatment. For example, to treat structural defects in articular cartilage, meniscus, and bone, the cell-seeded composite material (e.g. hydrogel) is placed at the defect site to promote repair of the damaged tissue.

In case of central nervous system (CNS) injuries, the material (e.g. hydrogel) can be seeded with a combination of adult neuronal stem cells, embryonic stem cells, glial cells and Sertoli cells. In the preferred embodiment, the composite scaffold can be seeded with Sertoli cells derived from transformed cell lines, xenogeneic or allogeneic sources in combination with neuronal stem cells. The Sertoli cells can be cultured with the composite scaffold for a period before addition of stem cells and subsequent implantation at the site of injury. This approach can circumvent one of the major hurdles of cell therapy for CNS applications, namely the survival of the stem cells following transplantation. A composite scaffold that entraps a large number of Sertoli cells can provide an environment that is more amenable for the survival of stem cells.

Accordingly, the material (e.g. hydrogel) can be effectively used as a raw material for fabricating artificial tissues or organs such as artificial blood vessels, artificial esophagus, artificial nerves, artificial hearts, prostatic heart valves, artificial skins, orthopedic implants, artificial muscles, artificial ligaments, artificial respiratory organs, etc. Further, the material (e.g. hydrogel) can be prepared in the form of a hybrid tissue by blending or incorporating on or into other types of biomaterials and with functional cells derived from tissues or organs. It may have various biomedical applications, for example, to maintain cell functions, tissue regeneration, etc.

In some embodiments, the material (e.g. hydrogel) as described above may be suitable the treatment of wounds. The wound healing material (e.g. hydrogel) will thus increases the rate of wound healing. The wound to be healed may be a result of a variety of acute or chronic internal or external injuries, diseases, or ailments, including, for example, abrasions, cuts, punctures, incisions, lacerations, ulcers, burns, surgical, bullet, bites, knife, or improvised explosive device induced wounds, and the like. The wound healing material (e.g. hydrogel) is thus sealed to the wound in a therapeutically effective amount to promote wound healing. The material (e.g. hydrogel) for the treatment of wounds may further comprise one or more additional components or agents, such as antibiotics or other antimicrobial compounds or agents and other agents known to improve wound healing.

In some embodiments, the material (e.g. hydrogel) as above described can be used to regenerate or repair cardiac muscle that has been damaged through age, disease, or degeneration. The affected area of the heart may include, for example, an area of the heart impacting cardiac function. Short and or long term ischemia can result in myocyte death, tissue infarction, and loss of contractile function. For example, the area to be treated may include ischemic penumbra or area best characterized as hibernating myocardium. Hibernating myocardium is a condition due to acute or chronic ischemia where certain portions of the myocardium exhibit abnormal or no contractile function but the cells remain viable. Accordingly the material (e.g. hydrogel) can be used, for example, in cardiac muscle regeneration for a number of principal indications: (i) acute heart attacks; (ii) therapy for congestive heart failure patients; (iii) prevention of further disease for patients undergoing coronary artery bypass graft; (iv) conductive tissue regeneration; (v) vessel smooth muscle regeneration; (vi) valve regeneration; and (vii) to wean patients from left ventricular assist devices implanted as a bridge to transplant and or destination therapy. Cardiac muscle normally does not have or has only limited reparative potential. In accordance with the method of the present invention, the material (e.g. hydrogel) as above described is sealed to the injured cardiac tissue the regenerate cardiac muscle in the subject. In this respect, a method is provided for regenerating or repairing cardiac muscle comprising adhering a material (e.g. hydrogel) as above described to a damaged or aged area of the heart with the nanoparticles of the present invention. The method is thus particularly suitable for improving ejection fraction (EF) and/or for decreasing the infarct size. By one approach, treatment of the heart as described herein may provide significant improvement in cardiac function such that no further treatment is necessary. By another approach, treatment of the heart may prolong survival of the subject prior to more radical therapy, including heart transplant.

In some embodiments, the material is a medical device. The medical device can be implanted at a variety of locations in the body including many different subcutaneous and sub-muscular locations.

In some embodiments, the medical devices include those used to sense and/or affect bodily function upon implantation and/or for carrying out various other functions in the body. These can be but are not limited to pacing devices, defibrillators, implantable access systems, monitors, stimulators including neurostimulators, ventricular assist devices, pain pumps, infusion pumps and other implantable objects or systems or components thereof, for example, those used to deliver energy and/or substances to the body and/or to help monitor bodily function. Representative examples include cardiovascular devices (e.g., implantable venous catheters, venous ports, tunneled venous catheters, chronic infusion lines or ports, including hepatic artery infusion catheters, pacemakers and pacemaker leads; neurologic/neurosurgical devices (e.g., ventricular peritoneal shunts, ventricular atrial shunts, nerve stimulator devices, dural patches and implants to prevent epidural fibrosis post-laminectomy, devices for continuous subarachnoid infusions); gastrointestinal devices (e.g., chronic indwelling catheters, feeding tubes, portosystemic shunts, shunts for ascites, peritoneal implants for drug delivery, peritoneal dialysis catheters, and suspensions or solid implants to prevent surgical adhesion); genitourinary devices (e.g., uterine implants, including intrauterine devices (IUDs) and devices to prevent endometrial hyperplasia, fallopian tubal implants, including reversible sterilization devices, fallopian tubal stents, artificial sphincters and periurethral implants for incontinence, ureteric stents, chronic indwelling catheters, bladder augmentations, or wraps or splints for vaso-vasostomy, central venous catheters; prosthetic heart valves, ophthalmologic implants (e.g., multino implants and other implants for neovascular glaucoma, drug eluting contact lenses for pterygiums, splints for failed dacrocystalrhinostomy, drug eluting contact lenses for corneal neovascularity, implants for diabetic retinopathy, drug eluting contact lenses for high risk corneal transplants); cochlear implants; otolaryngology devices (e.g., ossicular implants, Eustachian tube splints or stents for glue ear or chronic otitis as an alternative to transtempanic drains); dental implants, plastic surgery implants (e.g., breast implants or chin implants), catheter cuffs and orthopedic implants (e.g., cemented orthopedic prostheses). Implantable sensors for monitoring conditions such as blood pH, ion concentration, metabolite levels, clinical chemistry analyses, oxygen concentration, carbon dioxide concentration, pressure, and glucose levels are also included. Blood glucose levels, for example, may be monitored using optical sensors and electrochemical sensors.

For example, a pacemaker can be used to maintain a suitable heart rate and rhythm. Typically pacemakers are used to treat fainting spells (syncope), congestive heart failure, hypertrophic cardiomyopathy and other conditions. Different types of pacemakers include but are not limited to single chamber pacemakers; dual chamber pacemakers; and biventricular pacemakers.

A large variety of devices capable of providing stimulation to one or more parts of the body can be used in accordance with the present invention, and in the regard, the targeted implant location for these devices will vary depending on the application. Neurostimulation, muscular stimulation, gastric stimulation and/or other stimulation can be administered via electrodes on the leads and located within or proximate to the target tissue, organ or other body part or system. As examples, implantable medical leads may be positioned proximate to the vagal nerve for delivery of neurostimulation to the vagal nerve. Implantable neurostimulators can be used to send a stimulus, e.g., an electrical signal, via leads to the spine or brain to treat pain and other neurological disorders. Gastrointestinal conditions, severe chronic nausea and vomiting as well as urological disorders can also be treated with appropriate devices as will be understood by those skilled in the art. Chronic pain including back, neck and spinal pain can be treated as well using known devices. Epilepsy and essential tremor including tremors associated with Parkinson's disease and other neurological disorders can be treated in accordance with the present invention. If drug or other delivery systems are used, they will typically include a pump and a catheter for dispensing the substances.

The term "nanoparticles" means particles from 1 nm to 1000 nm, preferably from 2 to 500 nm and even more preferably from 5 to 300 nm in size. For most nanoparticles, the size of the nanoparticles is the distance between the two most distant points in the nanoparticle. For anisotropic nanoparticles, such as tubes whiskers or cylinders, the size of the diameter is the diameter of the smallest cylinder in which the nanoparticle is inscribed. Nanoparticle size can be determined by different methods such as Dynamic Light Scattering (DLS), Small Angle X-ray Scattering (SAXS), Scanning Mobility Particle Sizer (SMPS), Scanning Electron Microscopy (SEM), Transmission Electron Microscopy (TEM) (Orts-Gil, G., K. Natte, et al. (2011), Journal of Nanoparticle Research 13(4): 1593-1604; Alexandridis, P. and B. Lindman (2000), Amphiphilic Block Copolymers: Self-Assembly and Applications, Elsevier Science; Hunter, R. J. and L. R. White (1987). Foundations of colloid science, Clarendon Press.).

In some embodiments, the nanoparticles are selected among solid nanoparticles.

In some embodiments, nanoparticles can be inorganic, organic or mixed, and be coated or grafted.

The nanoparticles that are adsorbed on the surface may be made of different chemical nature, of different sizes, and/or of different shapes.

The nanoparticles can be in the form of a sphere, needle, flake, platelet, tube, fiber, cube, prism, whiskers or have an irregular shape.

Nanoparticles include without limitation the nanofibrils, nanochips, nanolatexes, nanotubes, expandable nanoparticles.

Among the mineral nanoparticles, one can mention metal oxides, alumina, silica, kaolin, hydroxyapatite, calcium carbonate, silicates such as micas quartz, zeolites or clays such as hectorite, laponite, montmorillonite, bentonite, smectite.

Mineral particles may include, but are not limited to, metal particles. Metal particles encompass particles formed exclusively with metallic alloys or metals chosen among alkaline earth metal, transitional metal, rare earth metal, and alloys thereof. In some embodiments, the metal may be aluminum, copper, cadmium, selenium, silver, gold, indium, iron, platinum, nickel, molybdenum, silicon, titanium, tungsten, antimony, palladium, zinc, tin, and alloys thereof. These metal particles may be metal organo modified nanoparticles having chemical entities grafted to their surface or having a self-assembled monolayer of compounds, such as organosulfur compounds, on their surface.

In some embodiments, particles may be particles of metal oxides, such as iron oxides (FeO, $Fe_2O_3$, $Fe_3O_4$), cerium oxide (CeO), alumina ($Al_2O_3$), zirconium oxide ($ZrO_2$), titanium oxide ($TiO_2$), titanates ($BaTiO_3$, $Ba0.5Sr0.5TiO_3$, $SrTiO_3$), indium oxide ($In_2O_3$), tin oxide ($SnO_2$), antimony oxide ($Sb_2O_3$), magnesium oxide (MgO), calcium oxide (CaO), manganese oxides ($Mn_3O_4$, $MnO_2$), molybdenum oxide ($MoO_3$), silica ($SiO_2$), zinc oxide (ZnO), yttrium oxide ($Y_2O_3$), bismuth oxychloride, Copper oxides (CuO, $Cu_2O$).

Particles may be metal carbides, nitrides, borides, sulphides and hydroxides.

They can also be organo-metallic nanoparticles: they are metal or metal oxide, carbides, nitrides, borides, sulphides and hydroxides nanoparticles, coated or grafted by an organic material.

Nanoparticles can be selected among metal inorganic salts: Inorganic salts include barium sulfate, calcium carbonate, calcium sulfate, calcium phosphate, magnesium hydrogen carbonate (including sugar moieties).

Nanoparticles can be selected among metal soaps derived from organic carboxylic acids having from 8 to 22 carbon atoms, preferably from 12 to 18 carbon atoms, for instance zinc stearate, magnesium or lithium stearate, zinc laurate, magnesium myristate.

Nanocomposite particles are included in the scope of the invention like for example core/shell metal/silica nanoparticles.

The particles can also be organic.

When the particle is organic, it is usually an organic polymer. Organic polymers encompass, but are not limited to, polystyrene, poly(vinyl acetate), poly(methylstyrene), poly(acrylamide), poly(acrylonitrile), poly(vinyl chloride), poly(butyl acrylate), poly(acrylic acid), copolymers of styrene and C1-C4alkyl (meth)acrylate, copolymers of styrene and acrylamide, copolymers of styrene and acrylonitrile, copolymers of styrene and vinyl acetate, copolymers of acrylamide and C1-C4 alkyl (meth)acrylates, copolymers from acrylonitrile and C1-C4 alkyl (meth)acrylate, copolymers of acrylonitrile and acrylamide, terpolymers from styrene, acrylonitrile and acrylamide, poly(methyl methacrylate), poly(ethyl methacrylate), copolymers styrene/butadiene, styrene/acrylic acid, styrene/vinylpyrrolidone and butadiene/acrylonitrile, or methoxy poly(ethylene glycol)-poly(lactide) copolymer (MPEG-PLA). Polymer particles can be crosslinked or not.

For instance, organic particles include, but are not limited to, nylon (for example marketed by ATOCHEM), polyethylene powders (for example marketed by PLAST LABOR), poly-2-alanine powders, polyfluorinated powders such as polytetrafluoroethylene (for example marketed by DUPONT DE NEMOURS), acrylic copolymer powders (for example marketed by DOW CHEMICA), polystyrene powders (for example marketed by PRESPERESE), polyester powders, expanded microspheres in thermoplastic material (for example marketed by EXPANCEL), microballs of silicon resins (for example marketed by TOSHIBA), synthetic hydrophilic polymer powders such as polyacrylates (for example marketed by MATSUMOTO), acrylic polyamides (for example marketed by ORIS), insoluble polyurethanes (for example marketed by TOSHNU), porous microspheres of cellulose, micro- or nanoparticles of PTFE (polytetrafluoroethylene).

In some embodiment, the nanoparticles are made of polysaccharides, i.e. molecules comprising two or more monosaccharide units. Typically the polysaccharide is selected from the group consisting of dextran, pullulan, agar, alginic acid, hyaluronic acid, inulin, heparin, fucoidan, chitosan and mixtures thereof. In a particular embodiment, the polysaccharide is a mixture of pullulan/dextran. Typically, the weight ratio of pullulan to dextran is 75:25 w/w. In another embodiment, the nanoparticles are made of hydroxyapatite—Pullulan/dextran polysaccharides as described in Example 4. Typically, the nanoparticles of polysaccharide are prepared according to WO/2012/028620.

In some embodiments, the nanoparticles are inorganic. Even more preferably, they are selected from: clays, silicates, alumina, silica, kaolin, carbon nanotubes cellulose nanocrystals, hydroxyapatite, magnetic nanoparticles like iron oxides, calcium carbonates, core-shell particles such as iron oxide core/silica shell particles. Small molecules or polymer chains can be grafted to stabilize nanoparticles in suspensions when necessary.

In some embodiments, at least one part of the nanoparticles are silica nanoparticles.

In some embodiments, the nanoparticles will act as contrast agents that can be directly imaged. The embodiment may find various applications. In particular, the contrast nanoparticles may tag the material and once implanted in the subject it will be possible to image it in vivo. In particular the embodiment offers the possibility for a structural or functional imaging procedure, e.g. for implanting the material in the subject with image guidance, for following the implantation of the material so as to verify that the maintenance of the material in the implantation site or to verify that the biodegradability of the material occurs. In particular, when the material shall be replaced because of dysfunction or time-limit expiration, the physician will have the opportunity to image it for analysing the implantation and then choose the best surgical procedure. Accordingly the nanoparticles can be detectable by imaging techniques such as ultrasonography, elastography, Supersonic Shear Wave Imaging, Magnetic Resonance Imaging (MRI), Positron Emission Tomography (PET), Single Photon Emission Computed Tomography (SPECT), fluorescence spectroscopy, Computed Tomography, X-ray radiography, or any combination of these techniques.

In some embodiments, the nanoparticles are designed to be detectable by x-ray imaging. In particular, the nanoparticles can be core and core-shell nanoparticles containing iodine for x-ray imaging as described in WO 2006106513. For example, it is possible to polymerize vinyl monomers carrying iodine-substituted side groups to form polymeric nanoparticles having considerable iodine content.

In some embodiments, the nanoparticles are designed to be detectable by Magnetic Resonance Imaging (MRI). MRI, which is an application of Nuclear Magnetic Resonance (NMR), has evolved into one of the most powerful non-invasive techniques in diagnostic clinical medicine and biomedical research. MRI has the advantage (over other high-quality imaging methods) of not relying on potentially harmful ionizing radiation. Thus, in some embodiments, nanoparticle comprises at least one paramagnetic metal ion. Examples of paramagnetic metal ions detectable by MRI are gadolinium III (Gd3+), chromium III (Cr3+), dysprosium III (Dy3+), iron III (Fe3+), manganese II (Mn2+), and ytterbium III (Yb3+). In certain preferred embodiments, the paramagnetic metal ion is gadolinium III (Gd3+). Gadolinium is an FDA-approved contrast agent for MRI.

In some embodiments, the nanoparticles consist of ultrasmall superparamagnetic iron oxide (USPIO) particles. USPIO particles are currently under investigation as contrast agents for imaging human pathologies (C. Corot et al., Adv. Drug Deliv. Rev., 2006, 56: 1472-1504). They are composed of a crystalline iron oxide core containing thousands of iron atoms which provide a large disturbance of the Magnetic Resonance signal of surrounding water. In contrast to other types of nanoparticles such as quantum dots (currently under investigation as extremely sensitive fluorescent probes), USPIO particles exhibit a very good biocompatibility. Chemical coating of USPIO particles is required to ensure their dispersion in biological media. Polysaccharides, such as dextran and its carboxymethylated derivatives, are currently used as coatings. USPIO particles are known in the art and have been described (see, for example, J. Petersein et al., Magn. Reson. Imaging Clin. Am., 1996, 4: 53-60; B. Bonnemain, J. Drug Target, 1998, 6: 167-174; E. X. Wu et al., NMR Biomed., 2004, 17: 478-483; C. Corot et al., Adv. Drug Deliv. Rev., 2006, 58: 1471-1504; M. Di Marco et al., Int. J. Nanomedicine, 2007, 2: 609-622). USPIO particles are commercially available, for example, from AMAG Pharmaceuticals, Inc. under the tradenames Sinerem® and Combidex®.

In some embodiments, the nanoparticles are designed to be detectable by fluorescence spectroscopy. Favorable optical properties of fluorescent moieties to be used in the practice of the present invention include high molecular absorption coefficient, high fluorescence quantum yield, and photostability. Preferred fluorescent moieties exhibit absorption and emission wavelengths in the visible (i.e., between 400 and 700 nm) or the near infra-red (i.e., between 700 and 950 nm). Selection of a particular fluorescent moiety will be governed by the nature and characteristics of the illumination and detection systems used in the diagnostic method. In vivo fluorescence imaging uses a sensitive camera to detect fluorescence emission from fluorophores in whole-body living mammals. To overcome the photon attenuation in living tissue, fluorophores with emission in the near-infrared (NIR) region are generally preferred (J. Rao et al., Curr. Opin. Biotechnol., 2007, 18: 17-25). The list of NIR probes continues to grow with the recent addition of fluorescent organic, inorganic and biological nanoparticles. Recent advances in imaging strategies and reporter techniques for in vivo fluorescence imaging include novel approaches to improve the specificity and affinity of the probes, and to modulate and amplify the signal at target sites for enhanced sensitivity. Further emerging developments are aiming to achieve high-resolution, multimodality and lifetime-based in vivo fluorescence imaging. Numerous fluorescent moieties with a wide variety of structures and characteristics are suitable for use in the practice of the present invention. Suitable fluorescent labels include, but are not limited to, quantum dots (i.e., fluorescent inorganic semiconductor nanocrystals) and fluorescent dyes such as Texas red, fluorescein isothiocyanate (FITC), phycoerythrin (PE), rhodamine, fluorescein, carbocyanine, Cy-3TM and Cy-5TM (i.e., 3- and 5-N,N'-diethyltetra-methylindodicarbocyanine, respectively), Cy5.5, Cy7, DY-630, DY-635, DY-680, and Atto 565 dyes, merocyanine, styryl dye, oxonol dye, BODIPY dye (i.e., boron dipyrromethene difluoride fluorophore), and analogues, derivatives or combinations of these molecules.

Nanoparticles which are used in the invention are selected as a function of the tissue nature or material. The nanoparticles should be capable of adsorption at the tissue or material surface. The selection of the appropriate nanoparticles suspension can be achieved by testing the nanoparticles affinity (adsorption) with the tissue or material. Briefly, a first method rests on Fourier transform infrared spectroscopy coupled with ATR. Attenuated total reflectance (ATR) is a sampling technique used in conjunction with infrared spectroscopy which enables sample surfaces to be examined. The detection and the quantification of adsorbed nanoparticles layer onto the tissue or material surface can be achieved. The proposed method consists in immersing the tissue sample or material into the nanoparticle solution or depositing a droplet of nanoparticle solution on the tissue surface, then the tissue sample or material is soaked and washed in a large volume of water during several days. Samples can be dried prior to ATR-FTIR analysis. The presence of an adsorbed nanoparticle layer on the tissue or material surface which persists after soaking enables to select the appropriate nanoparticles to use as adhesive. Conversely, the absence of nanoparticle at the tissue or material surface implies weak adhesive properties of the tested nanoparticles. Alternately, a second method rests on Scanning Electron Microscopy (SEM) in combination with Energy Dispersive X-ray (EDX). The tissue sample or material preparation is identical to the one disclosed above for the ATR-FTIR method. EDX is an analytical technique used for the elemental analysis or chemical characterization of a sample. The first micrometers of the surface are probed. Finally, with the method of thermal isotherms (Hourdet, D. and L. Petit (2010). Macromolecular Symposia. C. S. Patrickios. Weinheim, Wiley-V C H Verlag Gmbh. 291-292: 144-158.) the skilled professional can also determine comparatively the nanoparticles best suited for providing adhesion to a tissue surface or can carry out thermal isotherms adjusting pH to optimize adsorption mechanism, for example for anionic polyacrylic acid (PAA) macromolecules on the silica surface (Wisniewska, M. (2010) Journal of Thermal Analysis and calorimetry, 101(2), 753-760. doi: 10.1007/s10973-010-0888-4).

In some embodiments, the nanoparticles are applied on the surface as an aqueous suspension (or dispersion) of nanoparticles. Aqueous suspensions of nanoparticles are commercially available. One can mention the aqueous suspensions of colloidal silica Ludox® from Grace Davison. They can be prepared for any of the above-mentioned material by using methods known to the skilled professional Stöber et al. method (Controlled growth of monodisperse silica spheres in the micron size range, Journal of colloid and interface science (1968)). Advantageously, the aqueous suspension of nanoparticles which can be used according to the invention does not contain any other adhesive agent. It means that the aqueous suspension of nanoparticles does not contain a compound known as an adhering agent in a concentration that would allow it to play the function of adhesive agent. Among known adhesive agents, one can mention synthetic adhesives such as monomers, synthetic polymers (other than polymer nanoparticles), notably cyanoacrylates, urethanes, dendrimers; or natural adhesives such as fibrin, collagen, gelatin, and polysaccharides.

In some embodiments, the aqueous suspension of nanoparticles consists essentially of nanoparticles suspended in water. It means that other components can be present in the suspension, but they do not modify the properties of the suspension in a noticeable manner. Especially, other components can be present in the suspension, but they have to be selected so as not to modify the adhesive properties of the suspension (e.g. dispersion property of the nanoparticles).

In some embodiments, the nanoparticles are applied on the surface as a suspension containing a solvent, in particular an organic solvent. Said solution may suitable for improving suspension stability and for helping the particles to adsorb on the surface. The reason is that when the solvent evaporates (and/or penetrates a tissue or the material (e.g. a gel or a membrane or a film)) it leaves nanoparticles adsorbed onto the surface. The second role of the co-solvent that is not necessarily a good solvent of gel or tissue chains and thus it deswells the surface layer and favors gluing. Typically organic solvents include but are not limited to alcohols, diols and aprotic solvents. In a particular embodiment, the nanoparticles are deposited with a solution containing a mixture of water with an organic solvent. Typically the solution is an alcohol containing solutions or a solution containing mixture of water and alcohol. In particular, alcohol/water mixture can be used to disperse particles containing OH groups at the surface and can thus be useful to disperse organic tightly cross-linked degradable particles.

In some embodiments, the nanoparticles are applied on the surface as a powder. Typically excess of powder in the surface may be eliminated by peeling. It means that other components can be present in the powder, but they do not modify the properties of the powder in a noticeable manner. Especially, other components can be present in the powder, but they do not significantly modify the adhesive properties of the composition.

Typically, the preparation of nanoparticles suitable for dispersing the nanoparticles contains no more than 20%, or better, no more than 10% by weight of other adhering agent as compared to the weight of the dry matter of the composition, respectively aqueous suspension, preferably, less than 5% weight, even more preferably less than 2% and better less than 1%, even better, less than 0.5%.

However, materials distinct from the nanoparticles can be present in the preparation suitable for dispersing the nanoparticles, and notably mineral or organic ions can be present in the preparation. Among components that can be present in the preparation of nanoparticles, one can mention: mineral or organic ions, small organic molecules, proteins, physiological fluids. Notably, such components can be anti infectives, anti bacterians, preservatives, antibiotics, PEG, polymers of varied nature . . . . In some embodiments, the preparation of nanoparticles comprises an amount of pharmaceutical agent or a biological active agent as above described for the hydrogel.

According to the invention, the nanoparticles have the function of adhering agent in the compositions wherein they are present. Typically, in the preparations as above described, the nanoparticles represent from 10 to 100% by weight of the weight of the dry matter of the preparation. Typically, the nanoparticles represent from 20 to 100% by weight of the weight of the dry matter of the preparation, (e.g. the aqueous suspension), even more preferably, from 30 to 100%, and advantageously, from 40 to 100%, better from 50 to 100%, even better from 60 to 100%, preferably from 70 to 100%, even better from 80 to 100%, even more preferably from 90 to 100%. According to a particular embodiment, the nanoparticles represent from 95 to 100% by weight of the weight of the dry matter of the preparation, (e.g. the aqueous suspension), even better from 98 to 100%, and even more preferably from 99 to 100%.

Concentrations are adjusted to obtain suitable viscosities for application. In general suspensions of viscosity from about 10 Pa·s or less are used, preferably lower viscosities ($10^{-3}$ Pa·s). For non-spherical particles, like particles of CNT, or CNC type, the concentration is adjusted so that the viscosity remains fairly low.

The pH of the suspension of nanoparticles can be of any value from 1 to 14 and is adapted according to the application. pH can be adjusted to optimize adsorption, for example for anionic polyacrylic acid (PAA) macromolecules on the silica surface (Wisniewska, M. (2010), Journal of Thermal Analysis and calorimetry, 101(2), 753-760. doi:10.1007/s10973-010-0888-4) but also to keep the stability of the nanoparticles composition. For polyelectrolyte or amphoteric gels, the pH of the nanoparticles composition is adjusted to obtain nanoparticles of charges opposed to gel's charges.

Typically, the preparation of nanoparticles of the invention is applied using conventional techniques. Coating, dipping, spraying, spreading and solvent casting are possible approaches. More particularly, said applying is manual applying, applicator applying, instrument applying, manual spray applying, aerosol spray applying, syringe applying, airless tip applying, gas-assist tip applying, percutaneous applying, surface applying, topical applying, internal applying, enteral applying, parenteral applying, protective applying, catheter applying, endoscopic applying, arthroscopic applying, encapsulation scaffold applying, stent applying, wound dressing applying, vascular patch applying, vascular graft applying, image-guided applying, radiologic applying, brush applying, wrap applying, or drip applying.

In some embodiments, in particular for cutaneous application, the nanoparticles can be deposited on the tissue with means typically selected from the group consisting of a patch, a dressing, a elastoplasts or a band-aid having a plurality of capsules (e.g. nanocapsules) having the ability to release the nanoparticles (e.g. in the form of powder or a solution) when they are contacted by the tissue (e.g. because of a variation of temperature, physical pressure, osmotic pressure . . . ). Then after a while the means can be pull out, and the material or tissue can be approximated with the tissue where the nanoparticles were adsorbed.

The quantity of nanoparticles deposited at the surface of the tissue surface (or hydrogel) is from 0.1 mg/m$^2$ to 10 g/m$^2$. Depending on the size of the nanoparticles, the coverage of the surface is to be adjusted. These values can be from 1 mg/m$^2$, preferably for small particles, and up to 0.2 g/m$^2$, preferably for large particles. For large particles (typically of the order of 300 nm) the coverage is large, of the order of 4 g/m$^2$. For particles of smaller size (diameter of about 2 nm) rates coverage is preferably of the order of 10 mg/m$^2$. In particular, it is believed that optimum adhesion is obtained for a dense monolayer on the nanoparticles surface. The density of coverage can be evaluated on the assembly by ATR-FTIR or by SEM.

In some embodiments, the volume of nanoparticles that is deposited at the surface ranges from 0.01 to 5 µl. per mm$^2$. Typically, a volume of 0.1; 0.2; 0.3; 0.4; 0.5; 0.6; 0.7; 0.8; 0.9; 1; 1,1; 1,2; 1,3; 1,4; 1,5; 1,6; 1,7; 1,8; 1,9; 2; 2.1; 2.2; 2.3; 2.4; 2.5; 2.6; 2.7; 2.8; 2.9; 3; 3.1; 3.2; 3.3; 3.4; 3.5; 3.6; 3.7; 3.8; 3.9; 4; 4.1; 4.2; 4.3; 4.4; 4.5; 4.6; 4.7; 4.8; 4.9; or 5 µl per mm$^2$ is deposited at the surface.

In some embodiments, the nanoparticles are adsorbed in the two surfaces that shall be adhered (i.e. the two tissue surfaces, the tissue surface and the material surface). However, in a preferred embodiment only one surface is adsorbed with the nanoparticles. For example, when a material shall adhere to a tissue, it is preferable to absorb the nanoparticles on the material surface rather than on the tissue surface. In some embodiments, it may be desirable to get only one layer of nanoparticles.

In some embodiments, the approximating step is a manual approximating, a mechanical approximating, a suture approximating, a staple approximating, a synthetic mesh approximating, a biologic mesh approximating, a transverse approximating, a longitudinal approximating, an end-to-end approximating, or an overlapping approximating.

In some embodiments, the two tissue surfaces are approximated for a time ranging from 5 s to 2 min, preferably from 10 s to 1 min, more preferably from 20 s to 50 s. In particular, the 2 tissue surfaces are approximated during 20; 21; 22; 23; 24; 25; 26; 27; 28; 29; 30; 31; 32; 33; 34; 35; 36; 37; 38; 39; 40; 41; 42; 43; 44; 45; 46; 47; 48; 49; 50; 51; 52; 53; 54; 55; 56; 57; 58; 59; 60; 61; 62; 63; 64; 65; 66; 67; 68; 69; 70; 71; 72; 73; 74; 75; 76; 77; 78; 79; 80; 81; 82; 83; 84; 85; 86; 87; 88; 89; 90; 91; 92; 93; 94; 95; 96; 97; 98; 99; 100; 101; 102; 103; 104; 105; 106; 107; 108; 109; 110; 111; 112; 113; 114; 115; 116; 117; 118; 119; 120; 121; 122; 123; 124; 125; 126; 127; 128; 129; 130; 131; 132; 133 134 135 136 137 138 139 140 141 142 143 144 145 146 147 148 149 150 151 152 153 154 155 156 157 158 159 160 161 162 163 164 165 166 167 168 169 170 171 172 173 174 175 176 177 178 179 180 181 182 183 184 185 186 187 188 189 190 191 192 193 194 195 196 197 198 199 200 201 202 203 204 205 206 207 208 209 210 211 212 213 214 215 216 217 218 219

220 221 222 223 224 225 226 227 228 229 230 231 232 233 234 235 236 237 238 239 240 241 242 243 244 245 246 247 248 249 250 251 252 253 254 255 256 257 258 259 260 261 262 263 264 265 266 267 268 269 270 271 272 273 274 275 276 277 278 279 280 281 282 283 284 285 286 287 288 289 290 291 292 293 294 295 296 297 298 299 or 300 s.

In some embodiments, the nanoparticles are just absorbed on the surface of the material just before being applied to the tissue. Typically, the physician that would like to adhere a material on a tissue prepares the material as above described by adsorbing the nanoparticles to the surface of the material. Then he approximates the material and the tissue for a time sufficient for allowing the surfaces of the material and the tissue to adhere to each other.

In some embodiments, the nanoparticles are previously adsorbed on the surface of the material. Accordingly, the invention encompasses use of ready-to-use materials that can be prepared in an industrial manner and then be stocked in a proper manner. Once the clinician would like to use the material he has just to release the material and adhere it to the tissue without any preparation. For example, it is not necessary to hydrates the material before applying it to the tissue. The material, such as hydrogel can thus be applied directly to the tissue, and will automatically adhere to the tissue. For example the hydrogel will naturally swell in contact of the biological fluids present in the implantation site (e.g. blood, lymph, exudates . . . ).

Accordingly a further object of the invention relates to a material as above described wherein an amount of nanoparticles is adsorbed on at least one surface of the material.

The material is typically prepared as described above. For example, the material may be immerged in aqueous suspension of nanoparticles for a sufficient time for allowing the nanoparticles to adsorb to the surface of the material. Alternatively, an amount of nanoparticles are deposited on the surface of the material with a brush that was previously dipped in an aqueous suspension of nanoparticles. The aqueous suspension of nanoparticles may also be sprayed on the surface of the material. Then the material can be dried, optionally lyophilized (e.g. hydrogel), sterilized, packaged and properly stocked for a subsequent medical use. In some embodiments, a powder of nanoparticles is dispersed (e.g. by spraying) on the surface of the material and the excess is then washed. Then the material is optionally lyophilized (e.g. hydrogel), sterilized, packaged and properly stocked for a subsequently medical use.

Accordingly a variant of the method of the invention for adhering a material to a biological tissue in a subject in need thereof comprises the steps of providing the material wherein the nanoparticles were previously adsorbed in at least one surface and approximating the material and the biological tissue for a time sufficient for allowing the material and the biological tissue to adhere to each other.

As exemplified herein after the methods of the invention may find very various medical applications. In particular the methods of the invention provide the following advantages. First of all, the methods of the present invention may be used directly in vivo even in presence of body fluids such as blood, lymph, exudates, urine, bile, intestine contents . . . . Accordingly the methods of the present invention can be applied in tissue that are normally perfused or can be applied to tissues that are leaking (e.g. blood). In particular the inventors surprisingly demonstrate that nanoparticles can be adsorbed on the tissue surfaces in a sufficient manner for adhering even if a part of them is flowed by the presence of the body fluid, in particular blood. Secondly the methods of the present invention offer the advantage to maintain the physical, chemical and biological integrities of the tissue where the nanoparticles are adsorbed. In particular, as demonstrated by the inventors, no physical barrier is created (as generally observed with glues made of cyanoacrylate) that will prevent the tissue diffusion, e.g. the circulation of the biological molecules, cells (e.g. immune cells) or fluids between the adhering tissues or between the material (e.g. hydrogel) and the tissue. In particular, the physical properties of the tissue are maintained in particular the elasticity of the tissue. Thirdly the methods of the present invention are very easy to settle and may be performed very quickly in very different conditions (temperature, presence of body fluids, organ or tissues in motion (e.g. a beating heart) . . . ). The adhesion offer by the method of the invention may be a permanent adhesion or a temporary adhesion. For example, one skilled in the art can imagine that the methods of the invention may be performed during a surgery procedure so as to prevent in urgent manner a leaking of blood vessels till the surgeon stabilizes the haemostatic assembly with sutures, meshes or staples.

Accordingly in some embodiments, the methods of the invention are particularly suitable for sealing a defect between a first and second tissue in the subject.

In some embodiments, the methods of the invention are particularly suitable for providing a barrier to, for example, microbial contamination, infection, chemical or drug exposure, inflammation, or metastasis.

In some embodiments, the methods of the present invention are particularly suitable for stabilizing the physical orientation of a first tissue surface with respect to a second tissue surface.

In some embodiments, the methods of the present invention are particularly suitable for reinforcing the integrity of a first and second tissue surface achieved by, for example, sutures, staples, mechanical fixators, or mesh.

In some embodiments, the method of the invention of the present invention is particularly suitable providing control of bleeding.

In some embodiments, the methods of the present invention are particularly suitable for delivery of drugs including, for example, drugs to control bleeding, treat infection or malignancy, or promote tissue regeneration.

In some embodiments the methods of the present invention are particularly suitable in bariatric surgery, cardiac surgery, thoracic surgery, colon and rectal surgery, dermatologic surgery, general surgery, gynecologic surgery, maxillofacial surgery, neurosurgery, obstetric surgery, oncologic surgery, ophthalmologic surgery, oral surgery, orthopedic surgery, otolaryngologic surgery, pediatric surgery, plastic surgery, cosmetic and reconstructive surgery, podiatric surgery, spine surgery, transplant surgery, trauma surgery, vascular surgery, urologic surgery, dental surgery, veterinary surgery, endoscopic surgery, anesthesiology, an interventional radiologic procedure, an emergency medicine procedure, a battlefield procedure, a deep or superficial laceration repair, a cardiologic procedure, an internal medicine procedure, an intensive care procedure, an endocrinologic procedure, a gastroenterologic procedure, a hematologic procedure, a hepatologic procedure, a diagnostic radiologic procedure, an infectious disease procedure, a nephrologic procedure, an oncologic procedure, a proctologic procedure, a pulmonary medicine procedure, a rheumatologic procedure, a pediatric procedure, a physical medicine or rehabilitation medicine procedure, a geriatric procedure, a palliative care procedure, a medical genetic procedure, a fetal procedure, or a combination thereof.

In some embodiments, the methods of the present invention are particularly suitable in a dural repair, a nerve anastomosis, an endoscopic procedure, a skull base repair, a discectomy procedure, a fibrosis prevention after lumbar discectomy procedure, a scar formation prevention procedure, a posterior fossa procedure, an aneurysm repair, an arteriovenous malformation repair, a cerebrospinal fluid rhinorrhea prevention or repair procedure, a fusion procedure, a procedure to prevent fracture of weakened vertebral bodies, a procedure to repair disc herniation or to prevent the progression of disc herniation, a procedure to provide growth factors in spine surgery, a procedure to prevent or to manage dead space or seroma in spine surgery, an endoscopic neurosurgery or spine surgery procedure, or a procedure to repair an entrance portal in nucleoplasty.

In some embodiments, the methods of the present invention are particularly suitable for hernia repair. A hernia occurs when an organ, intestine or fatty tissue squeezes through a hole or a weak spot in the surrounding muscle or connective tissue. Hernias often occur at the abdominal wall. Sometimes a hernia can be visible as an external bulge particularly when straining or bearing down. The most common types of hernias are inguinal hernia which occurs in the inner groin, femoral hernia which occurs in the upper thigh/outer groin, incisional hernia which occurs through an incision or scar in the abdomen, ventral hernia which occurs in the general abdominal/ventral wall, umbilical hernia which occurs at the belly button and hiatal hernia which occurs inside the abdomen, along the upper stomach/diaphragm. Most hernias are caused by a combination of pressure and an opening or weakness of muscle or connective tissue. The pressure pushes an organ or tissue through the opening or weak spot. Sometimes the muscle weakness is present at birth but more often it occurs later in life. Anything that causes an increase in abdominal pressure can cause a hernia, including obesity, lifting heavy objects, diarrhea or constipation, or persistent coughing or sneezing. Poor nutrition, smoking, and overexertion can weaken muscles and contribute to the likelihood of a hernia.

In some embodiments, the methods of the invention are particularly suitable in a laparoscopic procedure, a hematoma, a subcutaneous flap, a mastectomy, an abdominopasty, a bowel resection, a bowel anastomosis, a thyroidectomy, an anastomotic leak after a gastric bypass procedure, a peritoneal adhesion prevention procedure, a burn injury, a fistula in ano, a pancreatic leak, a seroma after axial dissection, an intralesional support for tumor removal procedure, a spleen injury, an appendectomy, a cholecstectomy, a peptic or gastric ulcer repair procedure, closure of dead space to prevent a seroma in a general surgical procedure, fixation and sealing of the insertion site of a transcutaneous device, or a colostomy or other stoma procedure.

In some embodiments, the methods of the present invention are particularly suitable in a neck dissection, a tonsillectomy, an adenoidectomy, a tumor removal procedure, a frontal sinus repair, an endoscopic otolaryngologic procedure, or nasal septal surgery.

In some embodiments, the methods of the present invention are particularly suitable in a vascular graft procedure, an anastomotic bleeding repair procedure, a primary anastomosis, a percutaneous endovascular procedure, a prosthetic vascular graft procedure, a femoral artery repair, a carotid artery repair, attachment of endothelial cells to prosthetic grafts to create new endothelial lining, an endoscopic vascular surgery procedure, or an aortic reconstruction.

In some embodiments the methods of the present invention are particularly suitable in a joint replacement, a rotator cuff repair, a ligament repair, a tendon repair, a cartilage repair, attachment of cartilage cells and scaffold to a repair site, a meniscus repair, a labrum repair, a repair of lacerated or traumatized muscle tissue, treatment of a tendon or muscle strain, treatment of ligament sprain or overuse injury, an arthroscopic procedure, a tumor removal, a joint replacement revision, insertion and removal of an external fixator, a comminuted fracture stabilization procedure, a transcutaneous implant procedure (sealing of a pin insertion site to prevent entrance of bacteria), implantation of a bone stimulator, a bone graft procedure, a sports injury, a trauma procedure, a bone tumor removal procedure, a pubis symphysis separation repair, a slipped rib repair, closure of dead space to prevent a seroma in an orthopedic procedure, a fusion procedure, an open fracture repair, a closed fracture repair, treatment of growth plate disorders and slipped epiphysis, treatment of a bony defect, treatment of osteoporosis or osteopenia, a bone fixation procedure, fixation of trauma implants to bone, an endoscopic orthopedic procedure, or containment of bone fragments at fracture site with and without internal fixation.

In some embodiments, the methods of the present invention are particularly suitable in amniocentesis, premature rupture of amniotic membranes, an endoscopic obstetric procedure, or a cervical occlusion procedure.

In some embodiments, the methods of the present invention are particularly suitable in a Fallopian tube occlusion, a contraceptive procedure, a urinary incontinence procedure, a cystocoele repair, a rectocoele repair, a pelvic floor repair, a vulvo-vaginal reconstruction procedure, an amniotic membrane graft procedure, an endoscopic gynecologic procedure, or fixation of embryo transfer with in vitro fertilization.

In some embodiments, the methods of the present invention are particularly suitable in a pancreatic islet cell implantation, liver transplantation, kidney transplantation, pancreas transplantation, an endoscopic transplant procedure, or a combination thereof.

In some embodiments, the methods of the present invention are particularly suitable in balloon tracheal occlusion, closure of amniotic membranes, or a fetoscopic procedure.

In some embodiments, the methods of the present invention are particularly suitable in a pulmonary lobectomy, bi-lobectomy, sleeve lobectomy, bullectomy, segmentectomy, pulmonary wedge resection, an air leak, a tracheoesophageal fistula repair, a neotracheal reconstruction, a pleural leak, a thoracoscopic or bonchoscopic procedure, an endoscopic thoracic surgery procedure, closure of a tracheal or bronchial defect, or repair of a bronchopleural fistula. Thus the methods of the invention are particularly suitable in lung surgery. Types of lung surgery include lobectomy, lung biopsy, lung-tissue removal, and pneumonectomy. Risks associated with lung surgery include wound infection; post-surgical internal bleeding; air leaks; pain or numbness at the incision site; and infection of the lungs (pneumonia). Further, air leakage is frequently observed after thoracic procedures, such as pulmonary resection and decortication. It is important to create an air-tight seal so as to prevent or reduce severe complications, such as bronchopleural fistulas and infection resulting from extended chest tube drainage, extended recovery time, and postoperative morbidity related to pulmonary surgery. The method of the present invention is thus particularly useful for preventing some of the problematic aspects of lung surgery, such as treatment of pneumothorax and pulmonary leaks.

In some embodiments the methods of the present invention are particularly suitable in an ocular procedure, a retinal procedure, a retinal detachment procedure, a corneal repair, a glaucoma procedure, a glaucoma drainage device procedure, a laser procedure, a tissue flap procedure after laser surgery, a conjunctival repair, a pterygium repair, cataract surgery, repair of wet or dry macular degeneration, an endoscopic ophthalmologic procedure, or a sclera flap procedure.

In some embodiments, the methods of the present invention are particularly suitable in an oral wound closure, a tongue injury, a cheek injury, a tooth bed injury, a wisdom tooth removal, a root canal procedure, a bridge reconstruction procedure, a canker sore, a gum wound or graft procedure, removal of an oral tumor or other lesion, an endoscopic oral surgery procedure, or periodontal flap surgery.

In some embodiments, the methods of the present invention are particularly suitable in browplasty, a flap seroma repair, aesthetic surgery, a ptosis repair, rhytidectomy, a fasciocutaneous flap, body contouring surgery, a seroma after breast, face and body reconstructive surgery, a rhinoplasty, a skin graft to a wound or burn site, a muscle transfer to a wound site, a musculocutaneous flap, a decubitus injury, an ulcerative condition, a diabetic ulcer, a body contouring procedure, a liposuction procedure, a skin graft donor site repair, an endoscopic plastic surgery procedure, or a muscle transfer donor site repair.

In some embodiments, the methods of the present invention are particularly suitable in coronary artery anastomotic bleeding, a heart valve placement procedure, placement of a ventricular patch, control of bleeding from adhesions during a re-operative cardiac procedure, bleeding after a congenital heart defect repair, an endoscopic cardiac surgery procedure, or bleeding during and after cardiopulmonary bypass.

In some embodiments, the methods of the present invention are particularly suitable in an incontinence repair, a hypospadius repair, a fistula after hypospadius repair, a percutaneous nephrostomy, a percutaneous nephrolithotomy, a percutaneous nephrectomy, a vasovasotomy, a urinary fistula, a ureteral reconstruction, a circumcision, prostate surgery, vas deferens surgery, an anastomosis of the urethra, a stoma procedure, an endoscopic urologic procedure, or urologic trauma.

In some embodiments, the methods of the present invention are particularly suitable in an amputation, a tissue leak, a tissue perforation, a hematoma, a bleeding control procedure, a repair of luminal tissue, a tissue defect, a skin lesion, a topical wound closure, a microbial colonization or infection barrier procedure, a burn, a mucus membrane lesion, implantation of a pacemaker, implantation of a nerve stimulator, implantation of a pump, implantation of a bone stimulator, a fistula repair, a skin wound closure, a vascular access procedure, a percutaneous device procedure, or a periosteal flap.

The methods of the invention are particularly suitable for the treatment of skin lacerations. Skin lacerations are tears in the skin produced by accidents, trauma, or as a result of a surgical procedure. Lacerations often require treatment in order to close the hole in the skin, stop bleeding, and prevent infection. Accordingly, lacerations in the skin may be treated using the preparation of nanoparticles of the invention.

The methods of the invention are particularly suitable for the treatment of liver lacerations. Lacerations of the liver can occur from trauma or as a result of a surgical procedure. The liver is a highly vascularized organ and bleeds profusely when lacerated or traumatized.

The methods of the invention are particularly suitable in gastrointestinal anastomosis procedures. Gastrointestinal anastomosis is the technique of joining two pieces of bowel together. In particular, methods of the present invention could be used to supplement the sutures or staples used in intestinal anastomoses, providing a better seal that reduces leakage. Compositions and procedures for proper sealing the consequences of a failed anastomosis are severe and frequently life-threatening. Although failures can be caused by myriad factors, including poor surgical technique (e.g., sutures that were not inserted correctly; knots that were tied too tightly rendering the ends ischaemic; or incorrect use of a staple gun), the methods of the present invention should decrease or eliminate some of the causes of failed gastrointestinal anastomosis procedures.

The methods of the invention are particularly suitable in prostatectomy urethral-bladder anastomosis procedures. Prostatectomy urethral-bladder anastomosis is the technique of joining together a patient's ureter and bladder after surgical removal of his prostate gland. Failures are caused by myriad factors, including poor surgical technique (e.g., sutures that were not inserted correctly; knots that were tied too tightly rendering the ends ischaemic). The methods of the present invention are suitable to decrease or eliminate some of the causes of failed prostatectomy urethral-bladder anastomosis procedures.

The methods of the invention are particularly suitable for prosthetic dentistry. Replacement of teeth that are extracted or lost due to, mostly, periodontal disease, caries or trauma, can be performed with full dentures, partial dentures, bridges or implants. Accordingly the methods of the invention allow retention for prosthetic appliances.

The nanoparticles of the invention can be applied to two planes of tissue and then these two tissues can be sealed together. Over time the layer of nanoparticles degrades as new tissue grows into the area. Applications include a number of cosmetic and tissue restoration surgeries. The preparation of nanoparticles is used when the procedures involve significant tissue plane separation that may result in formation of seroma with associated complications, such as infection, e.g., general surgery procedures, such as mastectomies and lumpectomies, and plastic surgery procedures, such as abdominoplastys, rhytidectomy or rhinoplastys, mammaplasty and other cosmetic or reconstructive surgeries or procedures, forehead lifts and buttocks lifts, as well as skin grafts, biopsy closure, cleft-palate reconstruction, hernia repair, lymph node resection, groin repair, Caesarean section, laparoscopic trocar repair, vaginal tear repair, and hand surgery.

In some embodiments, the method of present invention is useful in sealing injection site wounds. Among the various possibilities, the injection can be given and then the nanoparticles to the injection site, or alternatively the nanoparticles can be applied and then the injection can be done through the layer of nanoparticles. In some embodiments, the invention relates to an aforementioned method, wherein said wound is in the eye. In some embodiments, the invention relates to an aforementioned method, wherein said wound is in the liver. In some embodiments, the invention relates to an aforementioned method, wherein said wound is in the lung. In some embodiments, the invention relates to an aforementioned method, wherein said wound is in the heart. In some embodiments, the invention relates to an aforementioned method, wherein said wound is the pancreas. In some embodiments, the invention relates to an aforementioned method, wherein said wound is in the dura matter. In some embodiments, the invention relates to an aforementioned method, wherein said wound is in an artery or vein. In some embodiments, the invention relates to an aforementioned method, wherein said wound is in cartilage. In some embodiments, the invention relates to an aforementioned method, wherein said wound is in a vertebral disk. In some embodiments, the invention relates to an aforementioned method, wherein said wound is in a sinus cavity. In some embodiments, the invention relates to an aforementioned method, wherein said wound is in or around the ear. In some embodiments, the invention relates to an aforementioned method, wherein said wound is of the type classified as a tissue plane. In some embodiments, the invention relates to an aforementioned method, wherein said wound is associated with a mastectomy. In some embodiments, the invention relates to an aforementioned method, wherein said wound is in the dura mater of the nervous system. In some embodiments, the invention relates to an aforementioned method, wherein said wound is in a cardiac artery or cardiac vein.

As used herein, the preparation of nanoparticles is a "treatment" when it improves the response of at least one biological tissue to which it is applied. In some embodiments, the improved response is lessening overall inflammation, improving the specific response at the wound site/interface of the tissue, enhancing healing, or a combination thereof. As used herein, the phrase "lessening overall inflammation" refers to an improvement of histology scores that reflect the severity of inflammation. As used herein, the phrase "improving the specific response at the wound site/interface of the tissue" refers to an improvement of histology scores that reflect the severity of serosal neutrophils. As used herein, the phrase "enhancing healing" refers to an improvement of histology scores that reflect the severity of serosal fibrosis.

In some embodiments, the methods of the present invention provide particularly advantageous applications in the treatment of loss of tissue architecture (including multiple cell types and matrix components precisely organized in three dimensions) caused for example by a trauma or a disease and which leads to loss of tissue function. It has been found that such loss of tissue architecture could be treated through generation of biological tissues involving the use of engineering and material methods to obtain the appropriate combination of cells and the suitable biochemical and physicochemical factors which mimic both the micro-environment of cells and the micro-architecture of tissue in the body. In this context, tissue engineering which aims to provide for biological substitutes which restore, maintain or improve tissue function or a whole organ has been developed. Typically, living cells are seeded onto biocompatible, and eventually biodegradable, scaffold and cultured in a bioreactor to lead to an initial cell population expanding into a tissue. With an appropriate scaffold which mimics the biological extracellular matrix, the developing tissue can adopt both the form and the function of the desired organ, and can be implanted into the body of patient. Moreover, the building of three-dimensional (3D) biological structures by the technology of Bioprinting is also possible ("Application of laser printing to mammalian cells", J. A. Barron, B. R. Ringeisen, H. Kim, B. J. Spargo, et D. B. Chrisey, Thin Solid Films, vol. 453-454, April. 2004, 383-387; "Quantification of the activity of biomolecules in microarrays obtained by direct laser transfer", V. Dinca, A. Ranella, M. Farsari, D. Kafetzopoulos, M. Dinescu, A. Popescu, et C. Fotakis, Biomedical Microdevices, vol. 10, October. 2008, 719-25). Bioprinting consists in an automated, computer-aided layer-by-layer deposition, transfer and patterning of biological materials including cells and cell aggregates ("Organ printing: computer-aided jet-based 3D tissue engineering", V. Mironov, T. Boland, T. Trusk, G. Forgacs, and R. R. Markwald, Trends in Biotechnology, vol. 21, April. 2003, 157-161; "Biofabrication: a 21<st> century manufacturing paradigm", V. Mironov, T. Trusk, V. Kasyanov, S. Little, R. Swaja, et R. Markwald, Biofabrication, vol. 1, 2009, p. 022001; "Jet-based methods to print living cells", B. R. Ringeisen, C. M. Othon, J. A. Barron, D. Young, et B. J. Spargo, Biotechnology Journal, vol. 1, September. 2006, 930-48). Recently, the use of bioprinting was enlarged to "the use of computer-aided transfer processes for patterning and assembling living and non-living materials with a prescribed 2D or 3D organization in order to produce bioengineered structures serving in regenerative medicine, pharmacokinetic and basic cell biology studies" (F. Guillemot, V. Mironov, M. Nakamura, Biofabrication, vol. 2, 2010). To this end, commercially available inkjet printers are used ("Application of inkjet printing to tissue engineering", T. Boland, T. Xu, B. Damon, and X. Cui, Biotechnology Journal, vol. 1, 2006, 910-917) ("Biocompatible inkjet printing technique for designed seeding of individual living cells", Makoto Nakamura, Akiko Kobayashi, Fumio Takagi, Akihiko Watanabe, Yuko Hiruma, Katsuhiro Ohuchi, Yasuhiko Iwasaki, Mikio Horie, Ikuo Morita, Setsuo Takatani, Tissue Eng 2006; "Delivery of human fibroblast cells by piezoelectric drop-on-demand inkjet printing", Saunders R E, Gough J E, Derby B., Biomaterials 2008; 29: 193-203.) to pattern biological assemblies according to a computer-aided design template. Pressure-operated mechanical extruders such as bioplotters have also been developed to handle live cells and cell aggregates ("Tissue Engineering by Self-Assembly of Cells Printed into Topologically Defined Structures", K. Jakab, C. Norotte, B. Damon, F. Marga, A. Neagu, C. L. Besch-Williford, A. Kachurin, K. H. Church, H. Park, V. Mironov, R. Markwald, G. Vunjak-Novakovic, and G. Forgacs, Tissue Engineering Part A, vol. 14, 2008, 413-421). Use of a laser-guided direct writing (LGDW) which is a technique capable of trapping multiple cells in a laser beam and depositing them as a steady stream onto arbitrary non-absorbing surfaces may be used ("Laser-guided direct writing for three-dimensional tissue engineering" Nahmias Y, Schwartz R E, Verfaillie C M, Odde D J, Biotechnol Bioeng 2005; 92: 129-36; "Micropatterning of living cells by laser-guided direct writing: application to fabrication of hepatic-endothelial sinusoid-like structures", Yaakov Nahmias, David J. Odde, Nat Protoc 2006).

Accordingly the methods of the invention are particularly suitable for building an assembly made with a multilayer of tissues and materials. The methods of the present invention may be indeed suitable for assembling the layer of tissues and material by adhering the tissue layers between them or for adhering the tissue layers to the adequate material(s). The methods of the invention are also particularly suitable for implanting said assembly in the subject by allowing the assembly to adhere to the targeted tissue.

The present invention relates to a kit for performing one method of the present invention, wherein said kit comprises an amount of nanoparticles.

In some embodiments, the kit comprises means for distributing the nanoparticles on the surface of the tissue and/or material (dripper, spray, vacuum, pipette or sealed pipette, patches, dressing, elastoplasts band-aid or brush for example).

In some embodiments, the kit of the present invention comprises a material as above described. Typically, the kit can comprise two or more compartments for separately conditioning the material and the amount of nanoparticles (e.g. in a form of an aqueous suspension) and for permitting an optimized use thereof. For example the kit can comprise a collection of material packaged in independent compartments and a flask comprising the nanoparticles with an appropriate distribution means (dripper, spray or brush for example). Alternately, it can comprise one material and the appropriate quantity of nanoparticles for adhering said material to a tissue surface.

In some embodiments, the kit of the invention comprises a material for which at least one surface was previously adsorbed with an amount of nanoparticles. Typically, the material was previously sterilized and packaged.

The invention will be further illustrated by the following figures and examples. However, these examples and figures should not be interpreted in any way as limiting the scope of the present invention.

FIGURES

FIG. 1. The preparation of nanoparticles and heart drug delivery system. A) A biodegradable porous polysaccharide 3D-matrix glued on rat heart. B) Macroscopic view after 3 days post-surgery. The 3D-matrix was still present glued on the heart and partially degraded as expected. Scale bar: 6 mm.

FIG. 2. Wound liver repair. A 1 cm transversal wound was made on the right lobe liver and then was bound with the preparation of nanoparticles. Macroscopic view after 3 days post-surgery of liver. The arrows shown a thin horizontal scar. No visible adhesions or inflammation were observed at the site of the injury.

FIG. 3. Peritoneum and mesh or drug delivery system. A crosslinked PVA sheet (A; blue arrows) or 3D-matrix (B; green arrow) was glued with a drop of the preparation of nanoparticles on parietal-peritoneum. C) PVA-sheet could not be removed by forceps. Scale bar: 6 mm.

FIG. 4. Effect of the preparation of nanoparticles on intestine. A 10 cm jejunum was harvested from rat (A), mounted on a plastic tube (B) and was cut into two parts (C). Then the preparation of nanoparticles was applied on the section (D), bounded together (D). After 1 minute, the system was removed from the container with a forceps. As shown in (E), the anastomosis was bounded by the preparation of nanoparticles.

FIG. 5. The preparation of nanoparticles in skin wound repair. A 1 cm length horizontal incision was made on both left side and right side of the dorsal midline with a scalpel. The edges of the wound were glued and sealed with the preparation of nanoparticles (left side) or sutured (Ethicon 4/0). At Day 3 post-surgery, no wound leakages, infection or inflammatory reactions were observed with the preparation of nanoparticles. The macroscopic skin scar are similar in both wound closure treatment.

FIG. 6. Effect of the preparation of nanoparticles on intestine small intestine. A piece of 10 cm jejunum was harvested from rat and cut in two parts. A first part was open and a drop of the preparation of nanoparticles was placed onto the last 2 cm of the intestine. Then 2 cm from the second intestine sample was applied to the preparation of nanoparticles. The two parts of tissue are stuck together and not separated in during the traction test.

FIG. 7. In order to evaluate the effect of the preparation of nanoparticles on spleen repair, the rat spleen removed and was cut vertically in two parts, then one section was coated with the preparation of nanoparticles and the two edges were brought together during 1 min. As shown in the figure, the two edges were glued together.

FIG. 8. shows the NP-glue or Fe2O3 NP-glue macroscopic final results.

FIG. 9. Hepatic resection. The right hepatic lobe was exposed (FIG. 9A) and a ⅔ of the lobe was totally transversally cutted (FIGS. 9B and 9C). The section was then covered by the NP-glue-coated PVA membrane (FIG. 9D).

Figure 16:
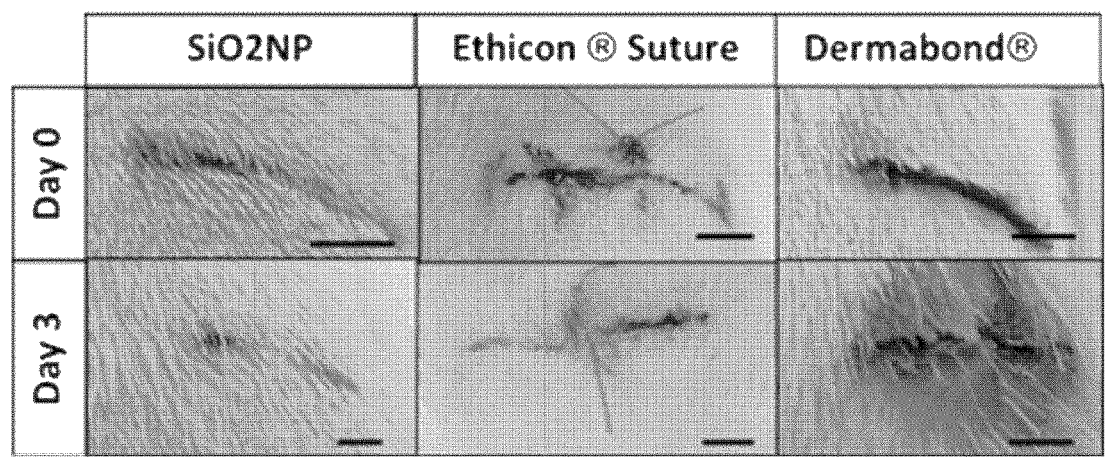

FIG. 16: Comparison of repair of full-thickness skin injury by SiO2NP nanobridging, by suturing, and by cyanoacrylate glue. Horizontal incisions were made at the dorsal face of rats with a scalpel. SiO2NP solution drop was put onto a wound edge with a brush and the two wound edges were gently pressed into contact for about a minute. The permanent closure was achieved within a minute. At day 3 post-surgery, no wound leakages, infection or inflammatory reactions were observed after nanobridging with SiO2NP. The other wounds were closed with a non-resorbable suture (Ethicon 4/0) and 2-octyl cyanoacrylate (Dermabond®). The rat skin closure quality achieved with nanoparticles and the suture were comparable. For the cyanoacrylate glue, the wound edges were not bonded correctly and an inflammatory skin reaction was noted at the time of the surgery for glue. Scale bars 0.5 cm.

Figure 17:
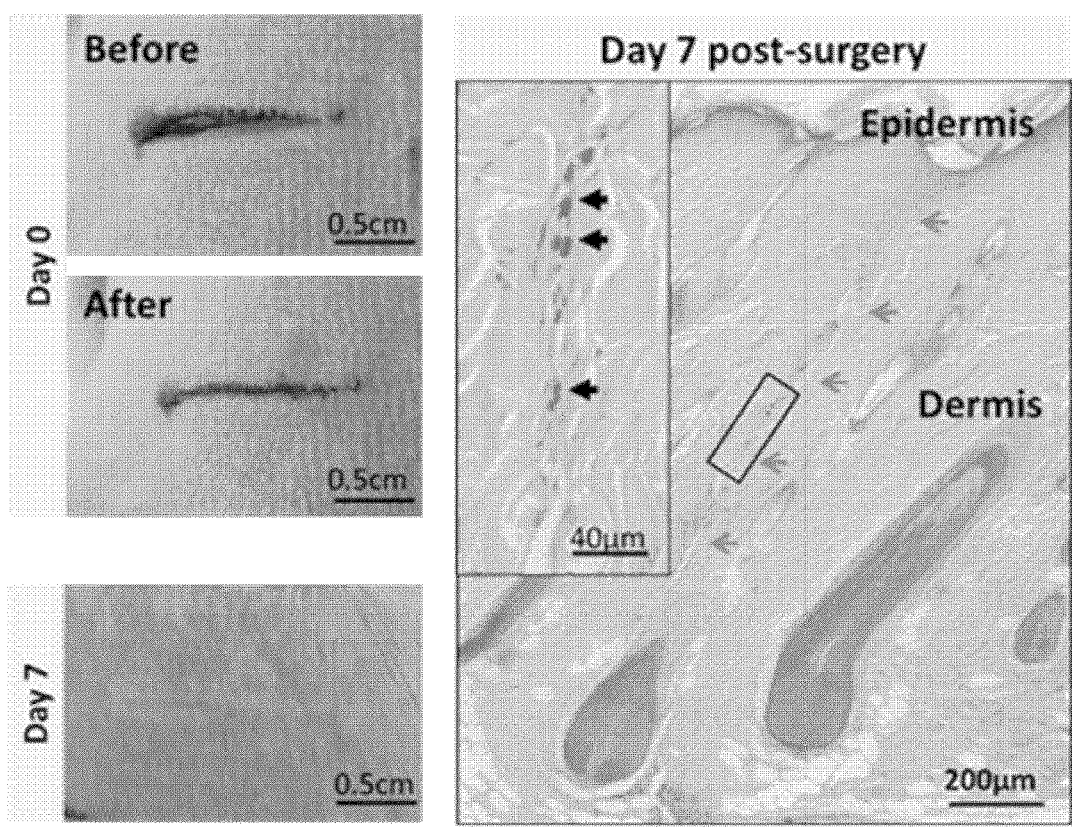

FIG. 17. Skin wound closure with Fe2O3NP solution. A full-thickness skin lesion was made at the dorsal face of rats and 4 µL of Fe2O3NP solution was soaked onto one edge of the wound. Two wound edges were gently pressed into contact for about a minute. A thin and aesthetic scar was observed. At day 7 post-injury, the histological sections stained with Hematoxylin Phloxin and Saffron evidenced the site of the injury as only a very thin line (blue arrows). Magnification (inset) of this area revealed a normal repair process and some particle aggregates along the wound closure.

Figure 18:
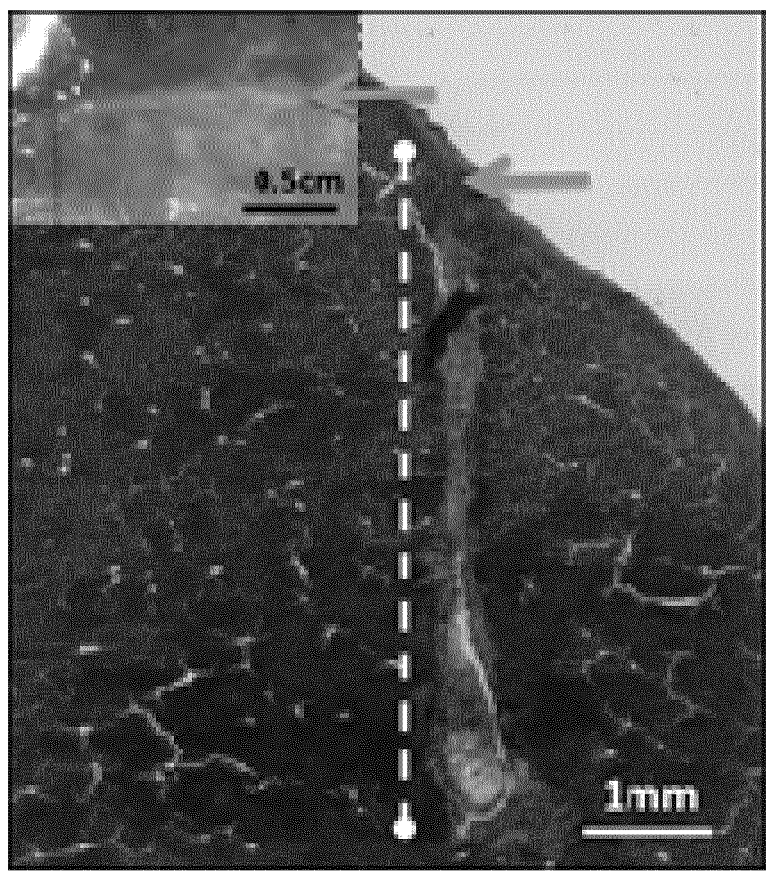

FIG. 18. Liver injury repair with Ludox® TM50 silica nanoparticles. A 6 mm deep horizontal incision was performed with a scalpel on a right hepatic rat lobe and nanoparticles solution was deposited to the bleeding injury with a pipette then the edges of the wound were brought together. After about 1 min, hemostasis was complete. Three days post-injury, macroscopic examination of the liver surface showed a thin fibrotic line at the site of the injury (Inset, blue arrows). Histological cross section of the wound (Hematoxylin Phloxin and Saffron stain), showed the formation of tissue repair from the liver surface (blue arrow) and along the wound (white dotted line)

EXAMPLE 1

Silica Particles TM50 Aqueous Dispersions

Silica Ludox® TM-50 water solutions with concentration of 52 wt % at pH 9 and SiO2/Na2O ratio of 200-250 and radius of about 15 nm, were purchased from Aldrich and used as received.

EXAMPLE 2

Silica Particles AL30 (Silica Used as a Powder and as a 30% Aqueous Solution)

Silica AL30 particles were synthesized by hydrolysis and condensation of tetraethylorthosilicate (TEOS, 99+%) following a procedure adapted from Stöber (Stöber, W., Fink, A. & Bohn, E. Controlled growth of monodisperse silica spheres in the micron size range. J. Colloid Interface Sci. 26, 62-69 (1968).). 600 mL of absolute ethanol and 36 mL of ammonium hydroxide solution (35 wt. % in water) were added to a round bottom flask and stirred for 5 min. 18 mL of TEOS were then quickly poured and the resulting solution was stirred overnight at room temperature. Silica particles were retrieved by centrifugation (7600 rpm, 45 min) and washed with absolute ethanol and followed by four cycles of centrifugation-dispersion. Silica particles were eventually air dried over 6 hrs at 80° C. Particles characterization was performed using dynamic light scattering (DLS) and transmission electron microscopy (TEM). The particles hydrodynamic radius (DLS) was 80 nm and the polydispersity index 15%. The radius determined from TEM images analysis was 50 nm.

DLS measurements were performed with an ALV/CGS-3 Compact Goniometer System equipped with a 22 mW HeNe Laser on diluted dispersion (2.7 mg/100 mL) in deionized water. The detection angle was varied from 30° to 150° with a 10° step. TEM images were obtained with a Zeiss CEM 902 microscope. The observation was made on a 1 wt. % dispersion in deionized water on a 400 mesh copper grid with a carbon film.

EXAMPLE 3

$Fe_2/O_3$ Nanoparticles $Fe_2O_3$ magnetic nanoparticles of 20-40 nm diameter and surface area equal to 30-60 $m^2/g$ were purchased from Alfa Aesar (Iron III oxide, magnetic NanoArc®) were processed with citric acid following a slightly modified procedure previously reported in the literature by Pinho et al. (*ACS Nano*, 2010, 4, 5339-5349).

In particular, 0.5067 g of $Fe_2O_3$ nanoparticles were dispersed in 8 mL of milli-Q water via ultrasonication for 5 minutes. The dispersion was subsequently transferred in a glass reactor equipped with a glass anchor-shaped stirrer that was preloaded with 100 mL of 0.02 M citric acid and was left under mechanical stirring overnight. Following the collection of the particles in a flask, they were decanted using a magnet and washed three times with milli-Q water. The citrated particles were re-dispersed in 12 mL milli-Q water via ultrasonication and were peptized via the addition of 40 µL of 35% w/w $NH_4OH$ aqueous solution. The pH of the supernatant solution measured using a pH meter paper was found to be between 7 and 7.5.

EXAMPLE 4

Nano-Hydroxyapatite Nanoparticles

Nano-hydroxyapatite nanoparticles suitable for tissue engineering, in situ tissue regeneration, as well as for drug delivery such as described in patent WO/2012/028620, PCT/EP2011/064924 for bone reconstruction and by J C Fricain et al. in Biomaterials 2013 Volume 34, Issue 12, April 2013, Pages 2947-2959 (A nano-hydroxyapatite— Pullulan/dextran polysaccharide composite macroporous material for bone tissue engineering). These nanoparticles can be used directly as components of NP-Glue alone, or on the surface of a medical device/biomaterial/tissue engineering product. They can be chemical modified or doped with several elements such as magnesium or strontium as reported by Brook I et al in J Biomater Appl. 2012 September; 27(3):291-8, or by Hao Y et al in J Nanosci Nanotechnol. 2012 January; 12(1):207-12.

Briefly, nHA is synthesized by wet chemical precipitation at room temperature. Fifty-nanometer nHA nanoparticles were obtained and characterized by using transmission electron microscopy, Fourier-transformed infrared spectroscopy and X-ray diffraction.

EXAMPLE 5

Liver Injury

Traumatic injury or surgery may trigger extensive bleeding. However, conventional hemostatic methods have limited efficacy and may cause surrounding tissue damage. For cyanoacrylate, the side effects include a systemic inflammatory reaction to foreign body, ie, pain and fever, local tissue necrosis and inflammatory reaction to foreign body, thrombo-embolic complications and septic complications. In addition, adherence of the needle to wall of varix and occlusion of the sclerotherapy catheter by residual adhesive has been reported. In contrast, fibrin sealants have the advantage of being biocompatible and biodegradable. The fibrin clot is resorbed as a part of the normal wound-healing process. As such, they are generally not associated with inflammation, foreign body reactions, tissue necrosis, or extensive fibrosis.

In this study, we use the preparation of nanoparticles of Example 1 to evaluate the ability of this device in hemostasis and liver or spleen tissue regeneration.

Both the procedure and the animal treatment complied with the Principles of Laboratory Animal Care formulated by the French National Society for Medical Research. Male Wistar rats (8 weeks) were anesthetized with sodium pentobarbital solution. A ventral midline laparotomy (5 cm) was performed. The right hepatic lobe was exposed and a 1 cm horizontal injury was performed with a scalpel and the preparation of nanoparticles was applied on the section. The two edges were brought together during 1 min and then the laparotomy was closed in two layers with a Vicryl 4/0. The animal was monitored during the acute post-surgery, in order to detect a bleeding syndrome. After 3 days post-surgery, animals were euthanized. The liver was exposed, photographed, and the injured area was removed with the surrounding tissue for histological studies.

Results: No inflammatory reactions or adhesions were observed after 3 days post-surgery. The emplacement of the injury was objective by a thin-scar line.

EXAMPLE 6

3D Scaffolds Fixation on Heart

The success of cell therapy depends of the ability to ensure the cell delivery within the target tissue. In cardiac or muscle ischemic injury, the research works aims to replace the cell lost. Genes, growth factors and cell-based therapies were developed. In cell-therapy, typical ways to deliver cells are intravenous, intracoronary or endocardial injection. In all case, a limited cell grafting is observed. To overcome this limitation, scaffold-delivery systems were developed. Scaffolds fixation to the infarct-area is a technical challenge. To avoid material slipping, the device was fixed to the heart with sutures or glue such as cyanoacrylate in function of the material composition.

In order to evaluate the ability of the preparation of nanoparticles to fix a scaffold to the heart and overcome the cytotoxicity of the cyanoacrylate glue, we implanted a 3D-biodegradable polysaccharide scaffold (Le Visage et al., Tissue Engineering 2012, 18(1-2):35-44) in beating heart position in rat with the preparation of nanoparticles of Example 1. In the previous study, the use of a scaffold promoted local cellular engraftment and survival but application was a main limitation in small and large animals (pig was tested).

Both the procedure and the animal treatment complied with the Principles of Laboratory Animal Care formulated by the French National Society for Medical Research. A 8 weeks Wistar rats were used for this evaluation. After anesthesia, tracheal intubation and mechanical ventilation, the thorax was open, the heart individualized. A 6 mm 3D-polysaccharide scaffold was glued with the preparation of nanoparticles onto the heart. The thorax was then closed (Ethicon 4/0). 3D-scaffold fixation was evaluated after 3 days.

After 3 days, the macroscopic evaluation does not evidenced inflammation. The 3D-scaffold was still visible onto the heart and the degradation of the polysaccharide scaffold occurred.

EXAMPLE 7

The Preparation of Nanoparticles Tissue Fixation

Intestine

Anastomotic leakage still remains a major complication in general surgery and can result in significant morbidity, mortality. Several patient related risk factors for leakage of intestinal anastomoses (corticosteroids, perioperative blood transfusion) or technical surgical factors (tight knotting of sutures, staplers, and intraluminal devices) have been identified to influence the outcome of gastrointestinal anastomoses. These considerations lead to the reinforcement of the anastomosis by glue. Tissue adhesive offers a reduction of suture material and, therefore, could ameliorate healing of intestinal anastomoses. Several studies already showed less inflammation and damage as well as a better blood supply in intestinal wound healing without sutures or staples. Different tissue adhesives were used but the outcome was poor due to their toxicity.

In order to evaluate the effect of the preparation of nanoparticles of Example 1 on intestine small intestine, a piece of 10 cm jejunum was harvested from rat and cut in two equal parts. A first part (5 cm length) was open and a drop of the preparation of nanoparticles was placed onto the last 2 cm of the intestine. Then 2 cm from the second intestine sample was applied to the preparation of nanoparticles. The two parts of tissue are stuck together and not separated in during the traction test.

Vessel

The same procedure was performed with vessel. The tissue was open and a drop of the preparation of nanoparticles of Example 1 was placed onto a piece of vessel. Then another part of vessel coated the preparation of nanoparticles. The two parts of tissue are stuck together and not separated in during the traction test.

Spleen Repair

In order to evaluate the effect of the preparation of nanoparticles of Example 1 on spleen repair, the rat spleen removed and was cut vertically in two parts, then one section was coated with the preparation of nanoparticles and the two edges were brought together during 1 min. As shown in the figure, the two edges were glued together.

EXAMPLE 8

Scaffolds Fixation onto Peritoneum

Abdominal wall repair by an open or laparoscopic approach is one of the most common operations performed in general surgery. Fixation of mesh is typically performed to minimize risk of recurrence either in open or laparoscopic hernia repair. Mesh fixation with staples has been implicated as a cause of chronic inguinal pain (0.7% to 62.9%). This related to reaction of suture fixation, displacement of the mesh. To overcome this side-effect, the use of adhesives for mesh fixation is increasing.

In order to evaluate the effect of the preparation of nanoparticles of Example 1 onto peritoneum, PVA scaffolds or 3D-polysaccharide matrix were fixed onto ex vivo parietal peritoneum abdominal wall with the preparation of nanoparticles. After 1 min, the scaffold and the 3D matrix could not be removed by the forceps.

EXAMPLE 9

Skin Wound Closure

Wound closure using suture materials is an integral part of the surgical process. Sutures are natural or synthetic textile biomaterials widely used in wound closure, to ligate blood vessels and to draw tissues together. Sutures consist of a fiber or fibrous structure with a metallic needle attached at one of the fiber ends and they can be classified into two broad categories: absorbable and non-absorbable. The most crucial requirements of sutures materials are physical and mechanical properties, handling properties, biocompatibility and antimicrobial nature and all these properties are inter-related. The choice of suture material also impacts on the wound healing process. One additional feature which is esthetically needed in the sutures is the scar prevention. Prevention of scarring is the major challenge to the wound healing process.

Bioadhesives (natural or synthetic materials) can be used for soft tissue repair to create a seal preventing leakage of biological fluids or to reinforce anatomic integrity. These products are widely used by many surgeons and some dermatological or plastics surgeons as an attractive alternative to sutures and staples, and a convenient and practical wound sealant.

Both the procedure and the animal treatment complied with the Principles of Laboratory Animal Care formulated by the French National Society for Medical Research. Adult Wistar male rats weighing 250 g (Wi/Wi, Charles-Rivers, France) were anesthetized by intraperitoneal injection of sodium pentobarbital solution (30 mg/kg, Centravet, France). The back was shaved, disinfected, and then draped in a sterile fashion. A 1 cm length horizontal incision was made on both left side and right side of the dorsal midline with a scalpel. The edges of the wound were glued and sealed with the preparation of nanoparticles of Example 1 (left side) or sutured (Ethicon 4/0).

The wound was observed after 1, 3 and 4 days after surgery. After 4 days, the rats were euthanized by an intraperitoneal injection of sodium pentobarbital (60 mg/kg) and the scar and the 0.5 cm of surrounding tissue was excised, gently rinsed in saline, fixed in a 4% paraformaldehyde solution, dehydrated, and embedded in paraffin. Seven-micron-thick sections were obtained (Leitz Wetzlar microtome, France), stained with Hemalun-eosin, and photographed using Q Capture Pro Software (Qimaging, Canada).

During the surgical procedure, the preparation of nanoparticles was easily applied on the wound. During the follow-up, no wound leakages, infection or inflammatory reaction were observed.

EXAMPLE 10

Preparation of Membranes

Figure 1:
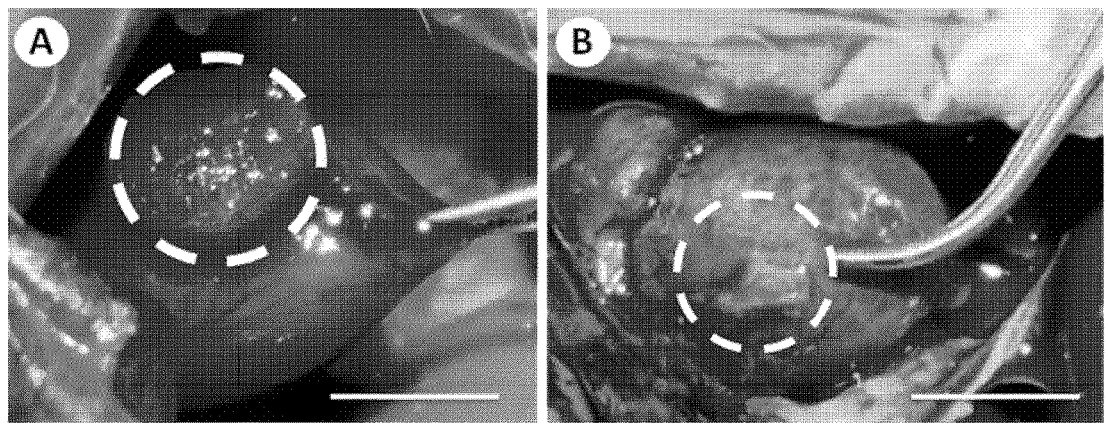
Figure 2:
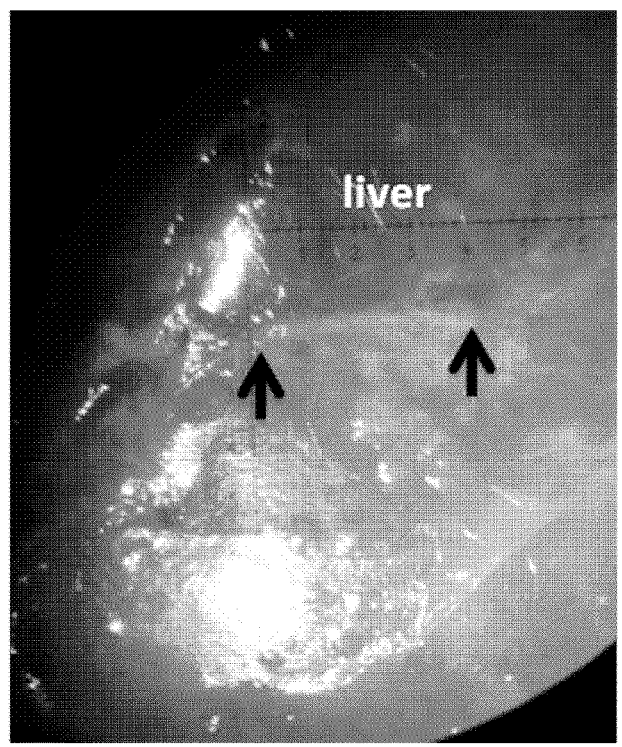
Figure 3:
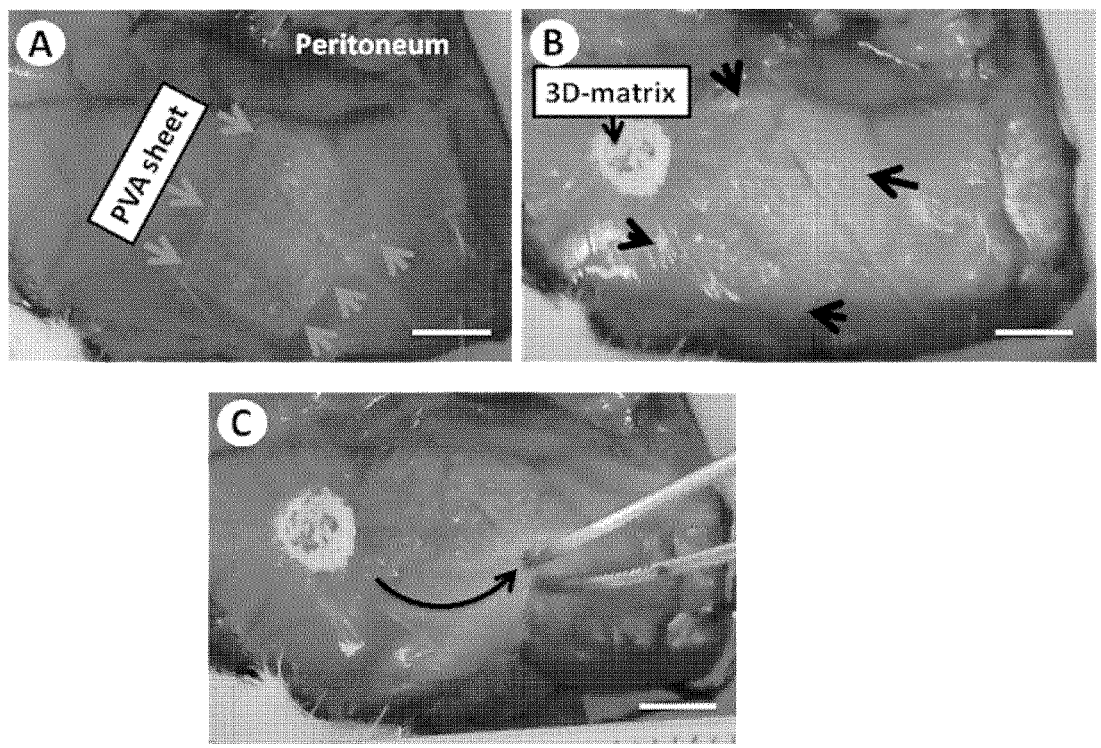
Figure 4:
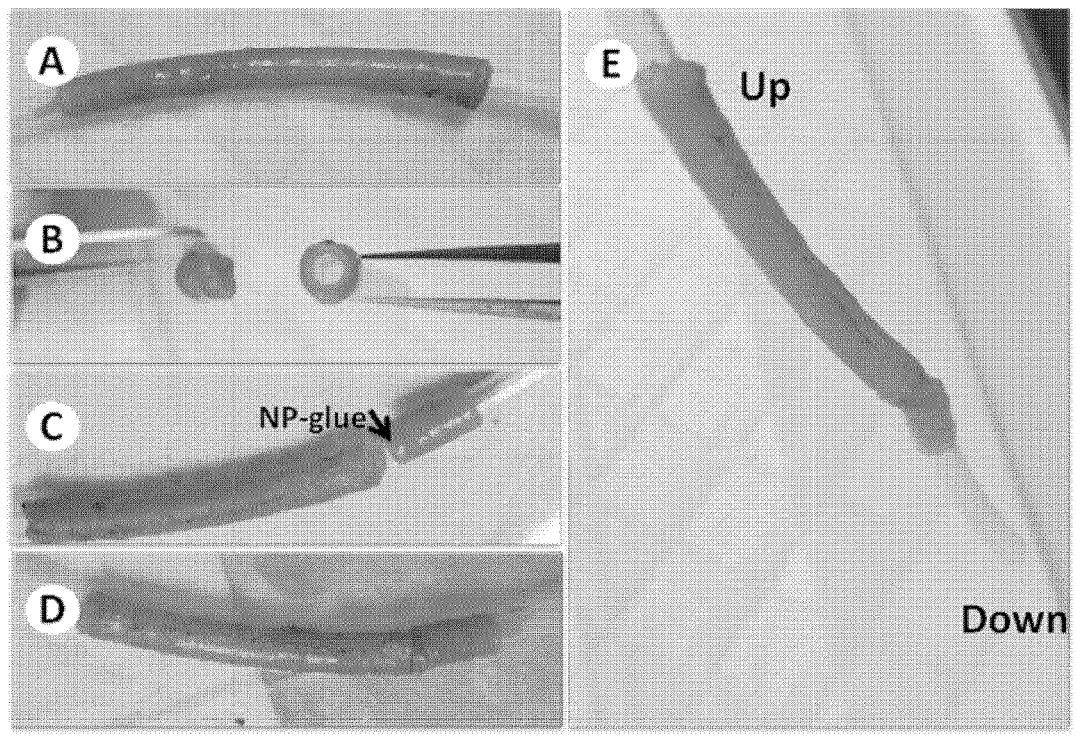
Figure 5:
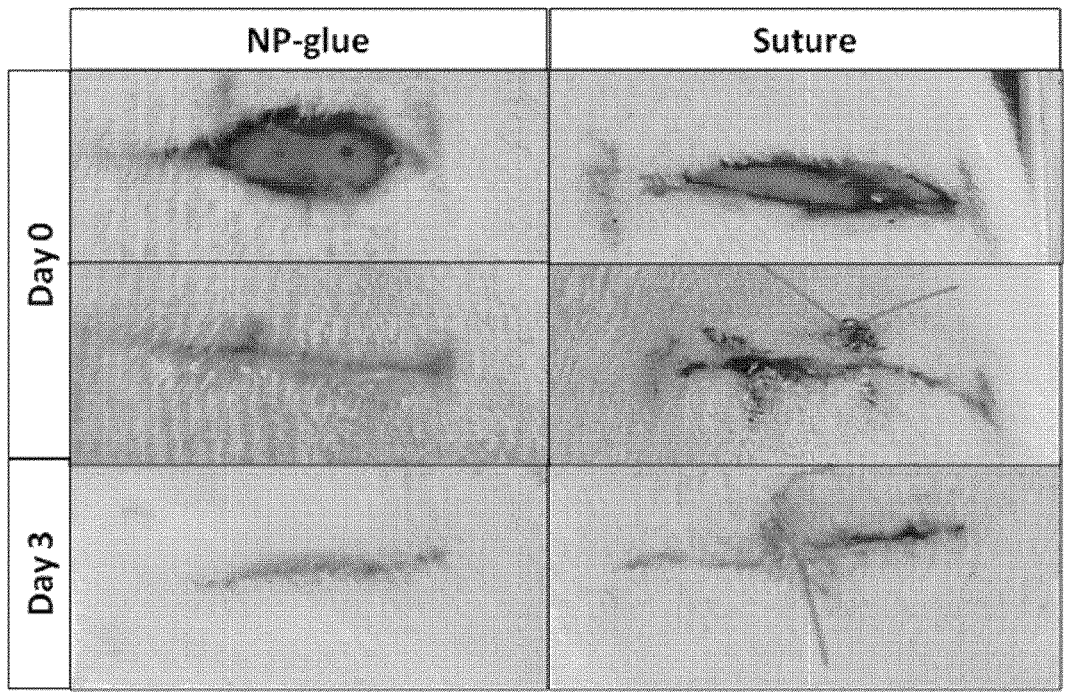
Figure 6:
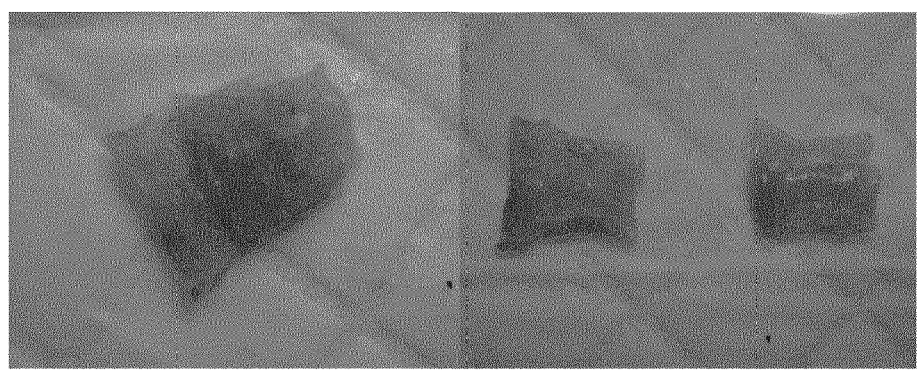
Figure 7:
Figure 8:
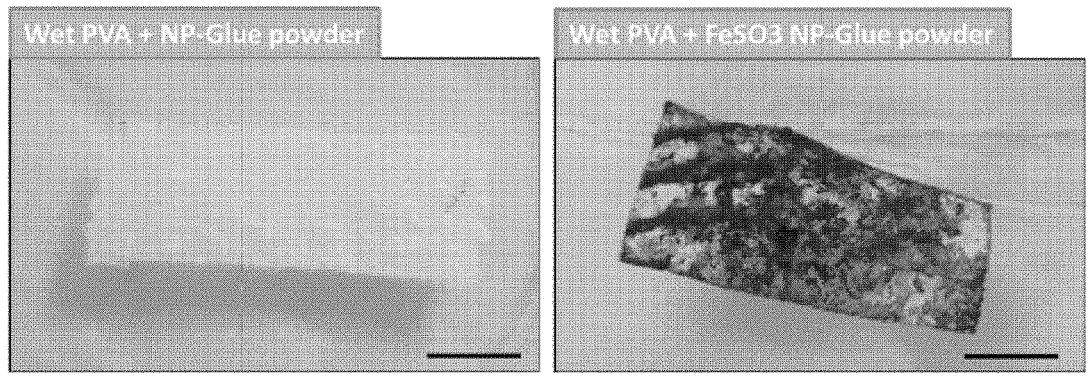

The NP-Glue powder (EXAMPLE 2) and the Fe2O3 NP-glue (EXAMPLE 3) were poured onto the wet PVA membrane. The powder in excess was removed by a gentle PVA/powder membrane shaking FIG. 8 shows the NP-glue or Fe2O3 NP-glue macroscopic final results.

EXAMPLE 11

Hepatic Resection

Hepatic resection has been increasing in frequency in the management of metastatic or primary neoplasms of the liver. Although mortality for this procedure has steadily decreased, the associated morbidity remains high. Morbidity is mainly associated with operative time and blood loss, especially in jaundiced and cirrhotic patients. During hepatic resection, control of bleeding from various sources is the most important problem faced by surgeons.

Figure 9:
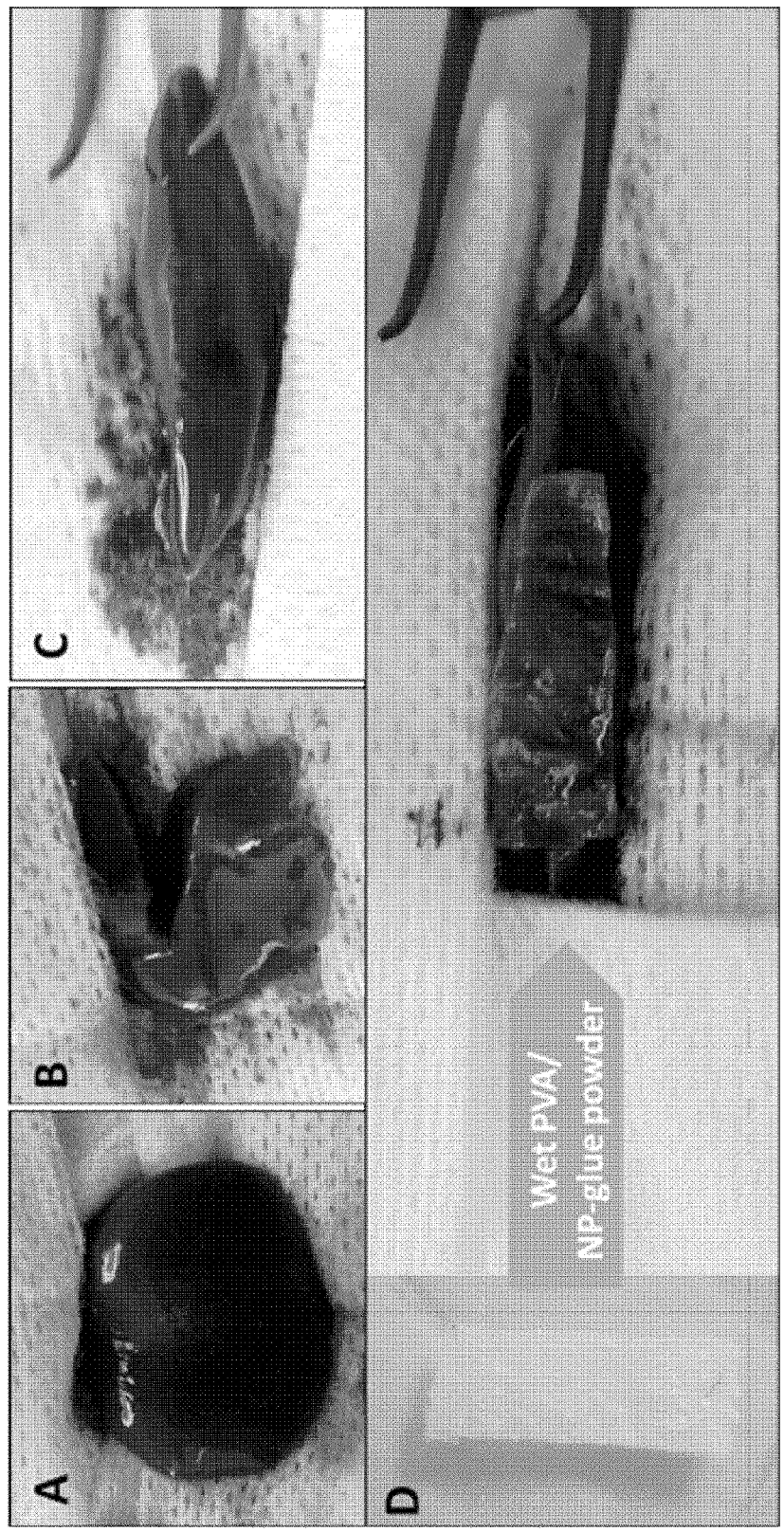
Figure 10:
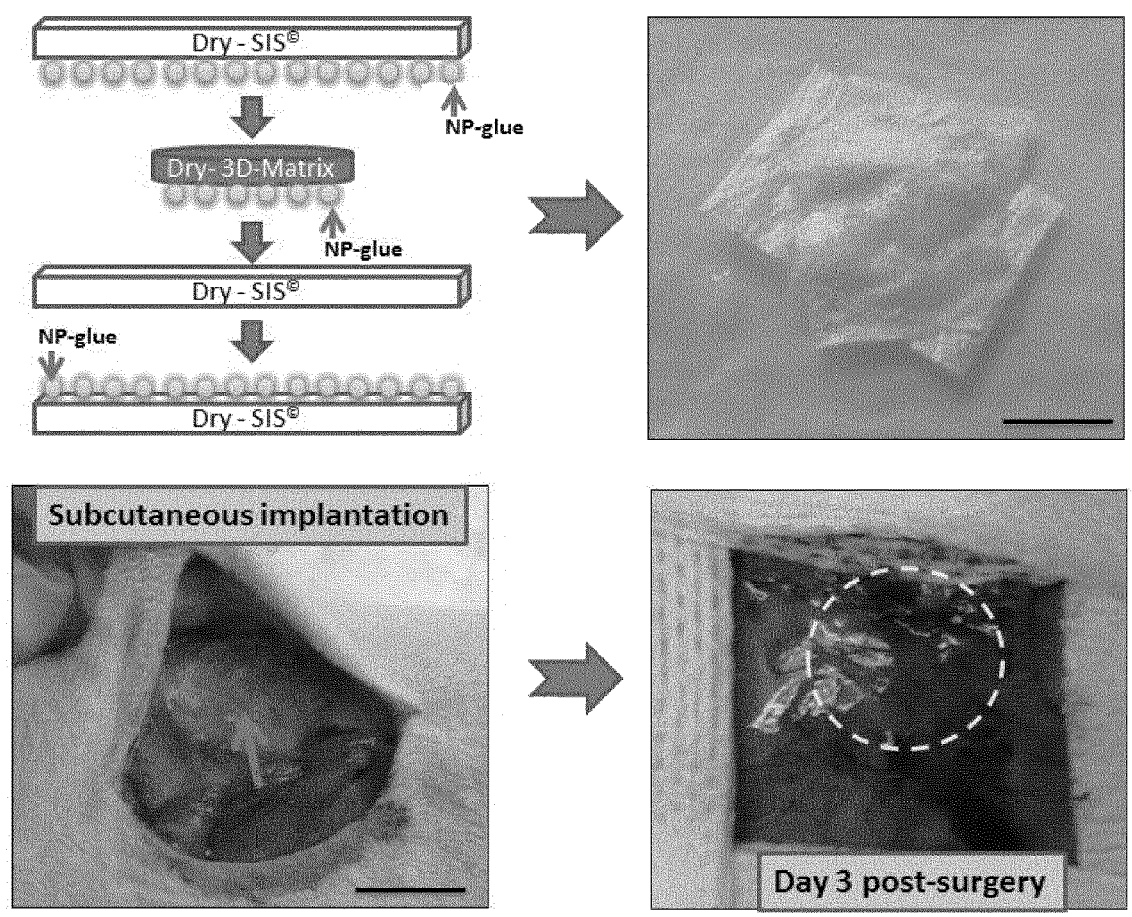
FIG. 10 shows a construction composed by 2 layers of SIS matrix, then a 3D-matrix, and a layer of SIS.

In this experiment, we evaluated the ability of a prepared NP-glue-coated PVA membrane (Example 9) to control the bleeding after the hepatectomy. Both the procedure and the animal treatment complied with the Principles of Laboratory Animal Care formulated by the French National Society for Medical Research. Male Wistar rats (8 weeks) were anesthetized with sodium pentobarbital solution. A ventral midline laparotomy (5 cm) was performed. The right hepatic lobe was exposed (FIG. 9A) and a ⅔ of the lobe was totally transversally cutted (FIGS. 9B and 9C). The section was then covered by the NP-glue-coated PVA membrane (FIG. 9D). The bleeding was evaluated and then, the laparotomy was closed in two layers with a Vicryl 4/0. The animal was monitored during the acute post-surgery, in order to detect a bleeding syndrome.

EXAMPLE 12

Preparation of a Multilayer

Tissue constructs are indicated for use in general surgical procedures for the reinforcement and repair of soft tissue where weakness exists, including, but not limited to, defects of the thoracic wall, suture line reinforcement, muscle flap reinforcement, hernia repair, soft tissue reconstructive procedures including plastic and reconstructive surgical applications, and for reinforcement of soft tissues which are repaired by suture or suture anchors.

They are also used in research 3D cell culture, in order to mimic the natural cell microenvironment, in biomaterial fields or in tissue engineering and regenerative medicine. Generally, a combination of cells/drugs and materials are needed to improve/replace the biological/physiological functions. One technical challenge is the fixation of these construct onto the target organ.

To evaluate the ability of the NP-glue (Example 2) to fix a 3D system, we elaborate a construction composed by 2 layers of SIS matrix, then a 3D-matrix, and a layer of SIS. The four layers are then bonded together with the NP-glue (Example 2), and implanted subcutaneously using NP-glue as a fixation system.

Figure 11:
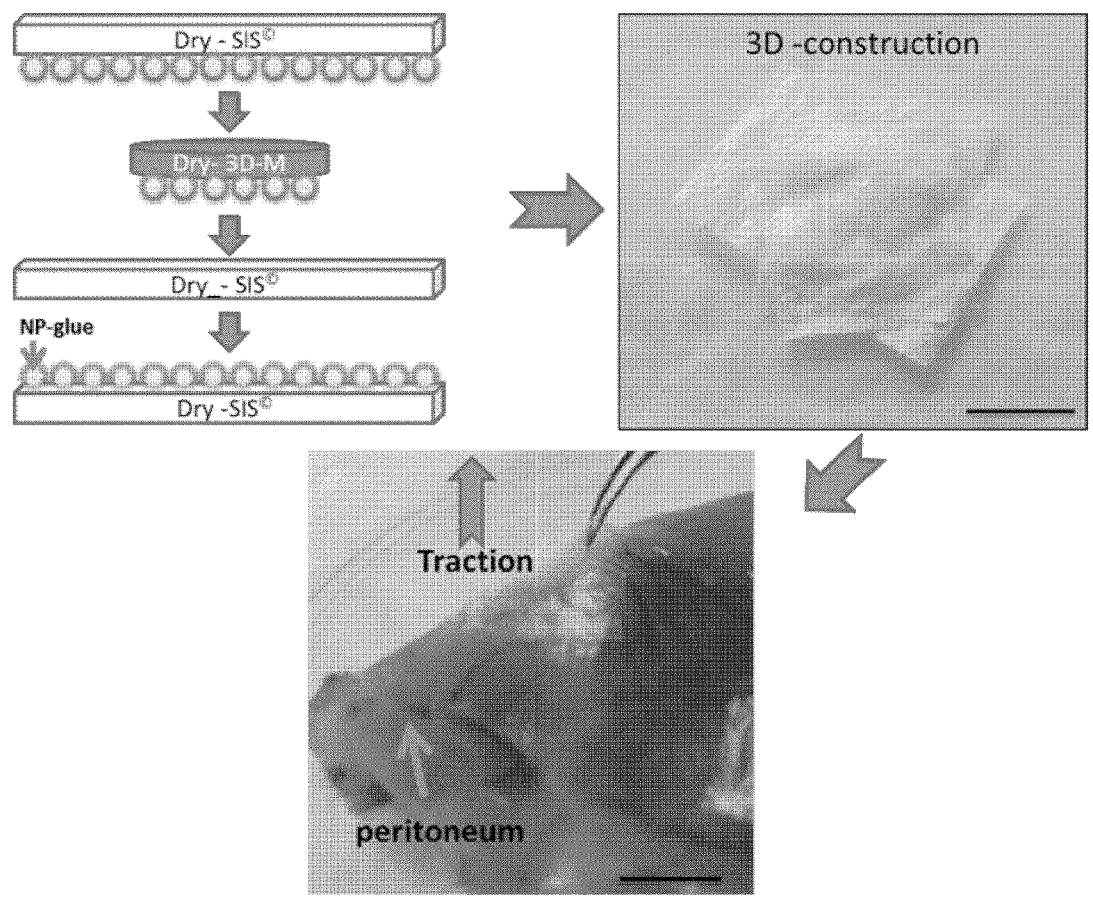
FIG. 11 shows that the traction of the construct of FIG. 10 with a forceps did not remove the structure.

The construct was then used in an ex vivo experiment. The device was glued onto the peritoneum with the NP-glue (Example 2). As shown in FIG. 11, traction with a forceps did not remove the structure.

Figure 12:
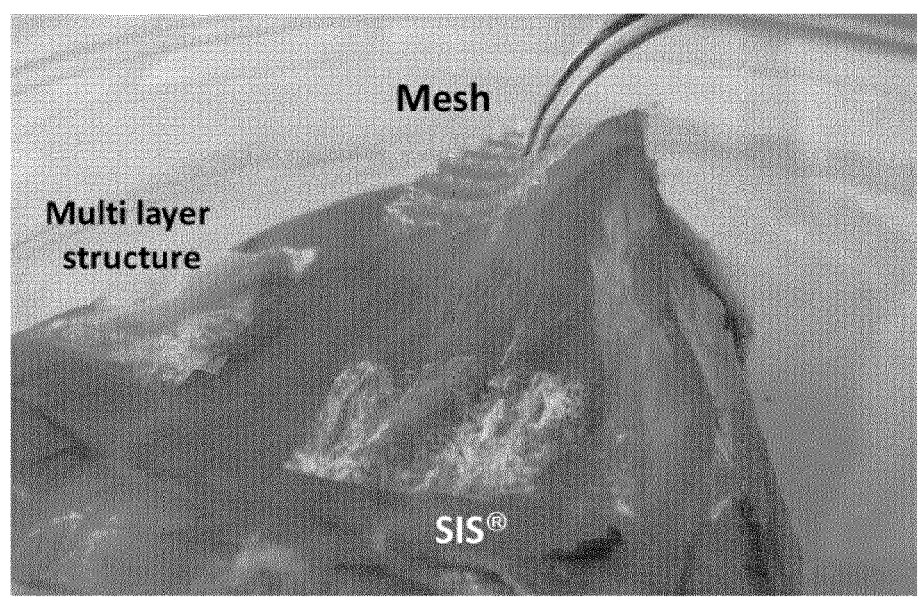
FIG. 12 shows the fixation of a mesh and a SIS® membrane.
Figure 13:
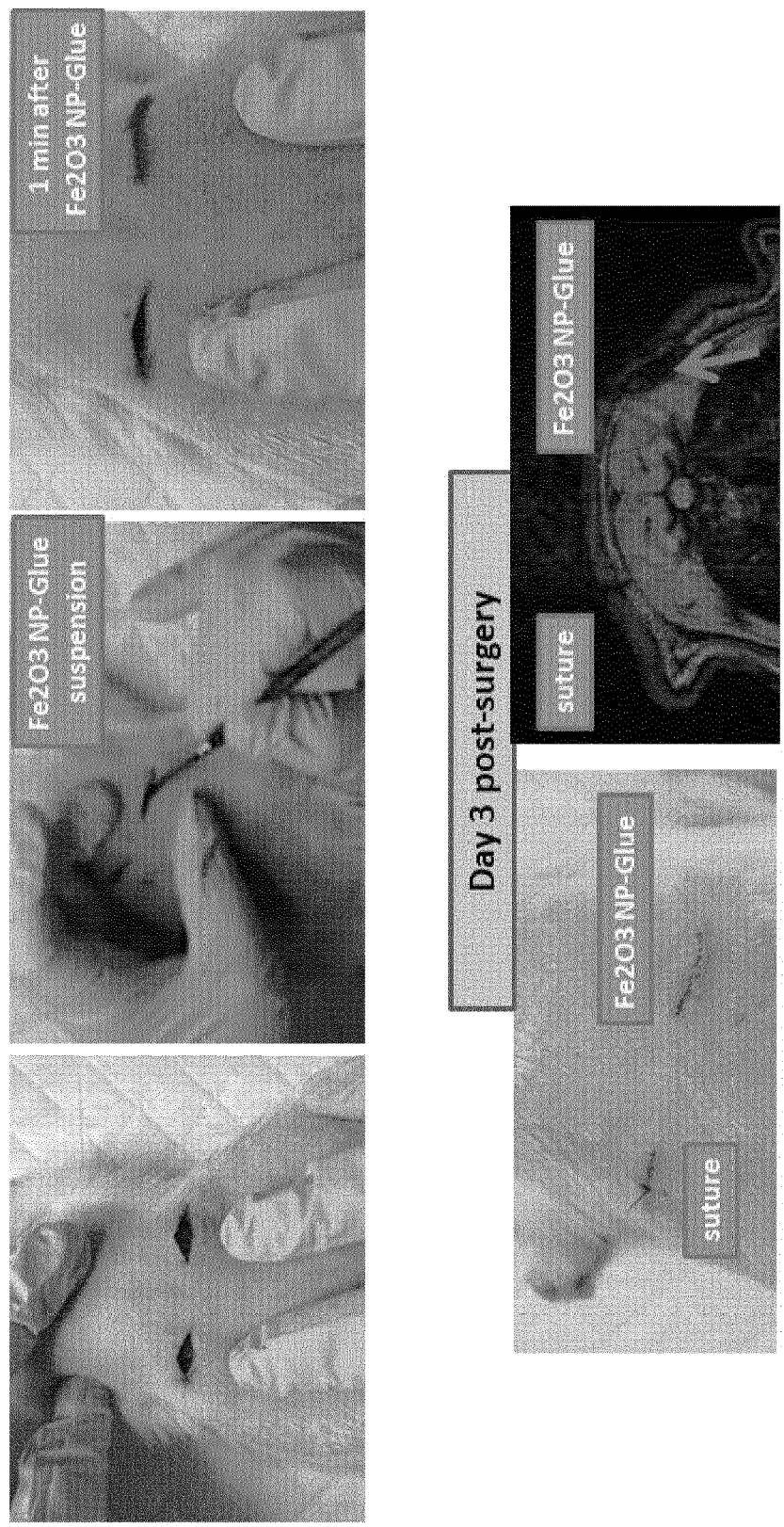
FIG. 13 shows the preparation of Fe2O3-nanoparticles in skin wound repair.

Same results were observed with mesh. For this experiment the mesh was glued with a NP-glue (Example 2) and then fixed onto peritoneum (FIG. 12). The same procedure was used for the SIS® membrane (FIG. 12).

EXAMPLE 13

Preparation of $Fe_2O_3$-Nanoparticles in Skin Wound Repair

Figure 14:
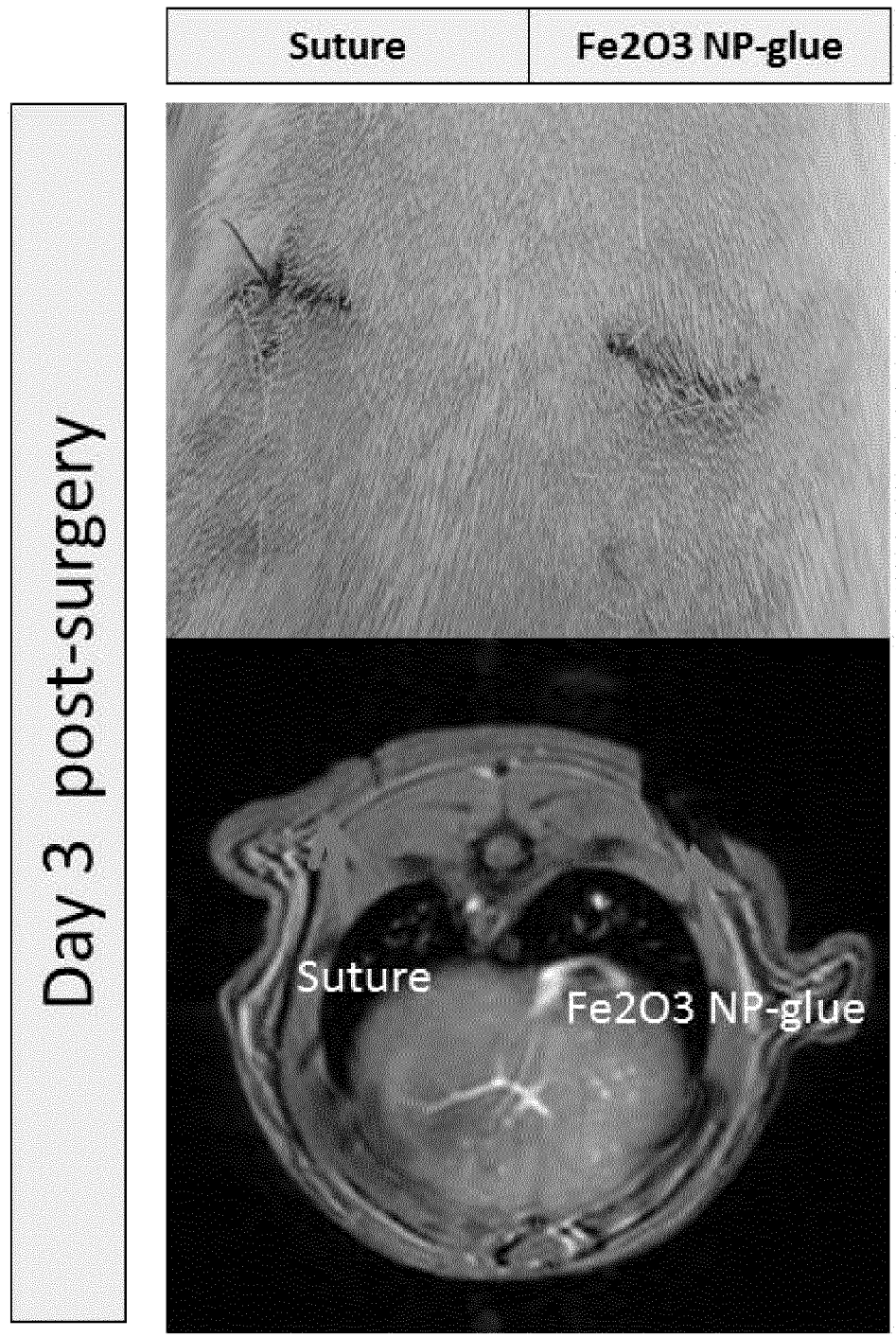
FIG. 14 shows that the Fe2O3 particles were observed at the site of the Fe2O3-treatment in comparison with the sutured-wound where no particles were shown
Figure 15:
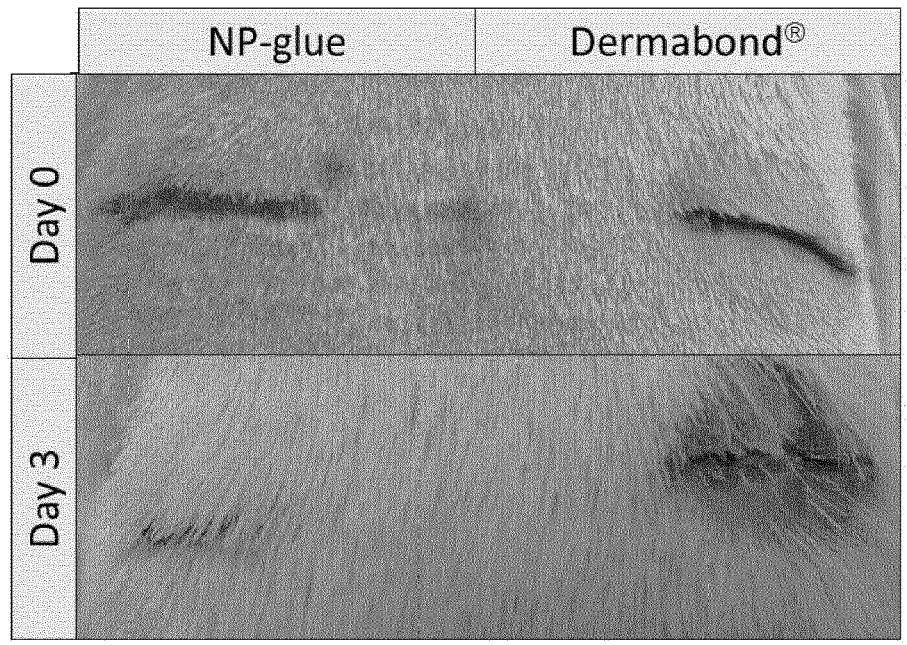
FIG. 15 shows the comparison of NP-glue and Dermabond® treatment in skin wound repair.

A 1 cm full-thickness length horizontal incision was made on both left side and right side of the dorsal midline with a scalpel. The edges of the wound were glued with a brush and sealed with the preparation of $Fe_2O_3$-nanoparticles of Example 3 (right side) or sutured (Ethicon 4/0). 1 min after particle deposition, the wound was sealed. At Day 3 post-surgery, no wound leakages, infection or inflammatory reactions were observed with the preparation of nanoparticles. The macroscopic skin scars were similar in both wound closure treatment and the Fe2O3 particles were observed with a 7 Tesla whole body MRI (blue arrow) (FIG. 14). The Fe2O3 particles were observed at the site of the Fe2O3-treatment in comparison with the sutured-wound where no particles were shown (FIG. 15).

EXAMPLE 14

Comparison of NP-Glue and Dermabond® Treatment in Skin Wound Repair

After a 1 cm full-thickness length horizontal incision, the wound were glued and sealed with nanoparticles (right side) or plastic surgery clinical (Dermabond®). At Day 3 post-surgery, an inflammatory reaction was observed with the clinical glue. In comparison, the treated wound preparation of nanoparticles was almost repaired.

EXAMPLE 15

Organ Repair, Hemostasis, and In Vivo Bonding of Medical Devices by Aqueous Solutions of Nanoparticles Experimental Section:
Silica SiO2NP nanoparticles were prepared using Stöber et al. method.[17] In particular 600 mL of absolute ethanol and 36 mL of ammonium hydroxide solution (35 wt. % in water) were added to a round bottom flask and stirred for 5 min. 18 mL of TEOS were then quickly poured and the resulting solution was stirred overnight at room temperature. Silica particles were retrieved by centrifugation (7600 rpm, 45 min) and washed with absolute ethanol and followed by four cycles of centrifugation-dispersion. Silica particles were eventually air dried over 6 hours at 80° C. Particles characterization was performed using dynamic light scattering (DLS) and transmission electron microscopy (TEM). The particles hydrodynamic radius (DLS) was 80 nm and the polydispersity index 15%. The radius determined from TEM images analysis was about 50 nm (Supporting Information, Fig. S4). The particles were dispersed in milli-Q waters at 30 wt %. Silica Ludox® TM-50 water solutions with concentration of 52 wt % of silica particles at pH 9 with particle radius of about 15 nm was purchased from Aldrich and used as received.

Iron oxide Fe2O3NP nanoparticle solutions were prepared using commercially available (NanoArc® purchased from Alfa Aesar) magnetic $Fe_2O_3$ nanoparticles of 20-40 nm diameter and surface area equal to 30-60 $m^2$/g. In particular, 0.5067 g of $Fe_2O_3$ nanoparticles were dispersed in 8 mL of milli-Q water via ultrasonication for 5 minutes. The dispersion was subsequently transferred in a glass reactor equipped with a glass anchor-shaped stirrer that was pre-loaded with 100 mL of 0.02 M citric acid and was left under mechanical stirring overnight. Following the collection of the particles in a flask, they were decanted using a magnet and washed three times with milli-Q water. The citrated particles were re-dispersed in 12 mL milli-Q water via ultrasonication and were peptized with 40 µL of 35% w/w $NH_4OH$ aqueous solution to obtain a 42.2 g/L concentration of the initial Fe2O3 particles. The pH of the solution measured using a pH meter paper was found to be between 7 and 7.5. Supporting Information Fig. S5 shows TEM image of Fe2O3NP nanoparticles.

Results and Discussion:

Stopping bleeding (hemostasis), preventing body fluid leakages, wound closing, and organ repair are everyday challenges in medical and surgical practice.[1] Sutures and staples are standard and efficient tools. Still, suturing can be demanding in inaccessible body regions or within minimally invasive surgery. Unfortunately, sutures are traumatic to tissues especially soft tissues such as liver[2], spleen[3], kidney[4] or lung[5]. During last decades synthetic or biological tissue adhesives that rely on in situ polymerization or cross-linking reactions emerge as a complementary technique.[1c, 6] However, tissue adhesives currently available in clinical practice present significant inherent limitations such as toxicity, insufficient strength and/or excessive swelling.[1c, 6c, 7] Biomimetic approaches and new chemistries that yield polymer materials with adaptable adhesion strength are under development.[6b, 6e, 8] In practice, gluing or sealing with polymers remains a complex process: it requires both stringent storage and preparation conditions before in vivo glue application or in vivo initiation and control of chemical polymerization or cross-linking reactions.

Recently, a novel approach to adhesion of hydrogels has been proposed.[9] It relies on the use of aqueous nanoparticle solutions in place of polymer adhesives. The method does not require a chemical reaction: a droplet of nanoparticle solution is spread on a gel surface and gel pieces are brought into contact. Nanoparticles, which are adsorbed to gel surfaces act as connectors between the pieces and assure adhesion. The adhesion strength is brought by macromolecules of the gel that are adsorbed onto the nanoparticles. Under constraint, adsorbed layers are able to reorganize, dissipate energy and prevent interfacial fracture propagation. The approach is not limited to synthetic hydrogels, and the adhesion was shown ex vivo for two slices of calf liver using a silica nanoparticle solution.

We propose that the principle of adhesion by particle nanobridging could be applied to wound closure. Nevertheless, decades of research on polymer tissue adhesives show how challenging it is to achieve an adequate adhesion in the presence of blood and this within a short time compatible with clinical practice. Moreover, adhesive joints have to withstand after closure constraints of in vivo conditions such as tissue motions or body fluids flow. Here, we demonstrate in vivo the applicability of silica nanoparticle aqueous solutions to repair in rats with two very different types of tissues such as skin and liver. We also show that iron oxide nanoparticles can be used to achieve strong and rapid wound closure and repair. Iron oxide nanoparticles are metabolized and, as an additional boon, they could provide a contrast in magnetic resonance imaging enabling clinical in situ observations.[10]

Wound closure is not the only area of applications that could benefit from adhesion brought by nanoparticles. For example, hepatic resection has been increasing in frequency in the management of metastatic or primary neoplasms of the liver. Although mortality for this procedure has steadily decreased, the morbidity mainly associated with operative time and blood loss remains high especially in cirrhotic patients. During hepatic resection, control of bleeding is a crucial problem faced by surgeons.[2, 5a, 7c, 11] We show here that particle nanobridging can provide means for rapid and permanent hemostasis after rat liver resection. To this end a polymer synthetic film was coated by nanoparticles by adsorbing nanoparticles onto its surface and spread to cover the intensely bleeding liver section. Strong adhesion and permanent hemostasis were achieved within a minute.

Similarly, to illustrate possibilities of nanobridging to attach prosthetic, medical and tissue engineering devices to organs in the wet and moving environment, we permanently fastened a 3D tissue-engineering scaffold to the beating rat heart using an aqueous solution of silica nanoparticle.

In order to optimize adsorption onto tissue surface it is advantageous to avoid using nanoparticles that are stabilized by polymer layers. Indeed, grafted or adsorbed polymers can be effectively repelled by intercellular (macro) molecules and thus prevent adsorption of particles onto tissue surface. Thus nanoparticles that have been optimized to circulate in the body are to be avoided. Two types of nanoparticles were thus used in this study. Silica nanoparticles (SiO2NP) with radius of about 50 nm were synthesized by Stöber method and applied as a solution in deionized water at concentration of 30 wt % (pH=8.5) or, when indicated, as a powder. Iron oxide $Fe_2O_3$ nanoparticles (Fe2O3NP) were purchased from Alfa Aeser, stabilized by citric acid, peptized and used in aqueous solution in milli-Q water at 42 g/L.

All procedures and animal treatment were in accordance with the Principles of Laboratory Animal Care issued by the National Society for Medical Research (authorization no. 006235 from French ministry of agriculture). For cutaneous wounds, the selection of the closure device depends essentially on the depth of the wound. For superficial lacerations, use of suture, adhesive tapes and cyanoacrylate adhesives such as 2-octyl-cyanoacrylate, N-butyl-2-cyanoacrylate-methacryloxysulfolane, N-butyl-2-cyanoacrylate) are the current methods of choice in humans.[1c] For deep wounds, closure suturing is the clinical gold standard (FIG. 16).[1a, 1b, 12] Indeed, cyanoacrylate adhesives cannot be properly used in this situation since they form a rigid joint and in contact with living cells they provoke local tissue reaction (toxicity and/or inflammation).

We anticipated that thanks to their size nanoparticles should not affect substantially the natural wound healing process and should not lead to formation of a rigid macroscopic barrier. We therefore aimed for repair by nanobridging of full thickness cutaneous incisions and compared resulting healing with that of sutured incisions in Wistar rats. Because the healing depends of the thickness of the skin and of the local skin state of tension,[1a, 13] we investigated an incisional wound model in two different sites: the thin abdominal skin and the thick dorsal skin and results were comparable.

Dorsal wounds of 1.5 cm in length and 3 mm in depth were nanobridged by Stöber silica (SiO2NP), commercial silica suspension Ludox TM50, or iron oxide (Fe2O3NP) nanoparticles solutions and compared to a standard suture by non-resorbable clinical thread (4/0, Ethicon) and commercial cyanoacrylate glues (Dermabond®, Histacryl®). Nanoparticle solutions were spread with a brush (n=6) or a micropipette (n=5) on one edge of the wound and two edges were brought together manually and pressed into contact. By using a micropipette, we could vary the volume of nanoparticle solution spread (from 2 µl to 15 µl). Excess solution, which rose to the wound surface, was removed with a compress. The wound edges were maintained in contact manually for less than one minute after which time the wound has closed. For all animals, wounds did not reopen during the follow up. The macroscopic results evidenced no pathological inflammation or necrosis (FIGS. 16 and 17). For all tested nanoparticles, scars were aesthetic, a feature which bodes well for many areas of skin surgery. Furthermore, nanobridging allows easily repositioning and adjusting wound edges to obtain an optimal alignment. Repositioning is in principle possible for suturing, but it requires removal of suture by trained personnel and increases operation time, adds local trauma that delays healing.

The presence of nanoparticles applied by brush or micropipette does not modify the first stages of healing process namely vascular clot formation and inflammation that prevent bleeding and remove cells and dying tissue.[14] As for sutures, the granulation tissue formed a new connective matrix serving as a migration structure for the cells. For Fe2O3 particles, Hematoxyline-Phloxine-Ponceau staining reveals the presence of small amount of aggregates (FIG. 17). Controlling particle aggregation is important. Indeed, when powders of silica nanoparticle rather than solutions were spread, the particle agglomerates limit the adequate wound closure and healing.

Cauterization, sutures or hemostatic sealants can treat surface lacerations of soft and wet tissues deeply penetrated by blood such as liver, spleen or kidney.[2, 11a-d, 11g] However, use of these techniques for deep wounds closure is very challenging. A 1.5 cm long and 6 mm deep horizontal incision on a right hepatic rat lobe was performed with a scalpel. To repair, $SiO_2$ or $Fe_2O_3$ nanoparticle solutions were deposited to the bleeding injury area with a pipette. The two edges of the wound were brought manually together and kept in contact. After about 1 min, hemostasis was complete and the injury stayed closed. In control experiments, the mechanical pressure did not lead to any permanent hemostasis in the absence of nanoparticle-solution. The rats were monitored during the acute post-surgery and no bleeding syndrome was detected (n=3). At day 3 post-surgery, stereomacroscopic observation of the liver showed a thin scar tissue (FIG. 18). Histological studies revealed the presence of thin granulation tissue between the two edges of the injury. Nanobridging not only assured hemostasis, biliostasis and wound closure, but also liver function that was not affected by the application of nanoparticle solutions. Alat and Asat enzymes were measured to be, respectively, 26 U/L and 81 U/L before surgery and 24 U/L and 74 U/L 3 days after repair by SiO2NP. The total bilirubin was in the normal range (1.4 µmol/L and 1.5 µmol/L, respectively, before and 3 days post-surgery).

For hemostasis after hepatectomy we propose employing nanoparticles in order to firmly attach membranes onto bleeding liver section. To illustrate the potential of such an approach we used a poly(vinylalcohol) (PVA) membrane with a surface coated with silica nanoparticles.[15] PVA film was swollen in phosphate buffer saline solution. The coating was realized by spreading SiO2NP powder on a surface of the swollen film. The unattached silica particles were removed by gently shaking the film. A ventral midline laparotomy (5 cm) was performed on a Wistar rat. The right hepatic lobe was exposed and resection of ⅔ of the lobe was totally transversally cut and the coated membrane was lightly pressed for few seconds against the bleeding section (FIG. 18). Hemostasis was immediately obtained. After 15 min of monitoring, the abdominal wall was closed with a Vicryl 4/0 and the rat was monitored during the acute post-surgery without any evidence of a bleeding syndrome. As shown in FIG. 18, neither pathologic inflammation nor bleeding was observed at the site of injury three days after surgery. In control experiments no hemostatic seal could be achieved with PVA membrane in the absence of $SiO_2$ coating.

For a membrane fixed onto a liver tissue to stop bleeding, the organ motions were limited. In many clinical situations, it is important to secure membranes, medical devices or tissue engineering constructs to organs that undergo important contractions such as the beating heart.[8a, 16] The application of adhesives is thus much more demanding and, when possible; suturing or cyanoacrylate glues are employed despite their toxicity and difficulty to apply at wet conditions. To check whether the adhesion brought by nanoparticles can withstand stringent in vivo conditions and prevent device slipping, we evaluated the ability of nanobridging to fix a scaffold onto the beating heart of rats. Rats were thus anesthesied and a tracheal intubation and mechanical ventilation were performed. The thorax was opened, and a drop of the silica Ludox® TM50 was spread on the surface of the heart with a brush. A 3D-scaffold of 6 mm in diameter made of a porous polysaccharide biodegradable hydrogel optimized for cell therapy [16] was brought into contact with the surface coated by nanoparticles and stayed firmly fixed resisting heart contractions and wet environment. After 3 days, the thorax was re-opened and the 3D-scaffold was still visible onto the heart (FIG. 19). The macroscopic evaluation does not evidence any sign of inflammation and as expected the degradation of the polysaccharide scaffold started to occur.

In summary, we demonstrated that rapid and strong adhesion by aqueous solutions of nanoparticles can be advantageously used in very different clinical situations. For skin wounds a remarkable aesthetic healing was obtained and repair procedure does not require any specific preparation or training Bleeding control and tissue repair by nanobridging shown here in the case of liver could be used on spleen, kidney, heart, and lungs surgeries. When tight sealing is needed nanobridging could complement anastomosis and classical suturing protocols. The possibility of securing medical devices could open new applications in repair and regenerative medicine. From chemistry standpoint, the principle illustrated here is not limited to silica and iron oxide nanoparticles and they are many possible choices of sizes, forms and surface chemistries. In particular, nanoparticles with intrinsic biological effects such as silver nanoparticles for skin infection or drug delivery systems could provide useful options. Translation to clinical practice will require careful safety and toxicity investigations. A better understanding of biological mechanisms of the adhesion by nanobridging will guide the design of future-generation tissue adhesives.

REFERENCES

Throughout this application, various references describe the state of the art to which this invention pertains. The disclosures of these references are hereby incorporated by reference into the present disclosure.

[1] a) J. Armitage, S. Lockwood, *Surgery (Oxford)* 2011, 29, 496-501; b) H. K. Kjaergard, *Am J Surg* 2001, 182, 15S-20S; cW. D. Spotnitz, S. Burks, *Transfusion* 2012, 52, 2243-2255.
[2] R. L. Reed, 2nd, R. C. Merrell, W. C. Meyers, R. P. Fischer, *Ann Surg* 1992, 216, 524-538.
[3] S. Uranus, H. J. Mischinger, J. Pfeifer, L. Kronberger, Jr., H. Rabl, G. Werkgartner, P. Steindorfer, J. Kraft-Kirz, *World J Surg* 1996, 20, 1107-1111; discussion 1111-1102.
[4] S. Siemer, S. Lahme, S. Altziebler, S. Machtens, W. Strohmaier, H. W. Wechsel, P. Goebell, N. Schmeller, R. Oberneder, J. U. Stolzenburg, H. Becker, W. Luftenegger, V. Tetens, H. Van Poppel, *Eur Urol* 2007, 52, 1156-1163.
[5] a) S. Canonico, *Acta Biomed* 2003, 74 *Suppl* 2, 21-25; b) K. D. Murray, C. H. Ho, J. Y. Hsia, A. G. Little, *Chest* 2002, 122, 2146-2149.
[6] a) A. P. Duarte, J. F. Coelho, J. C. Bordado, M. T. Cidade, M. H. Gil, *Progress in Polymer Science* 2012, 37, 1031-1050; b) M. Mehdizadeh, J. Yang, *Macromol Biosci* 2013, 13, 271-288; c) M. Ryou, C. C. Thompson, *Techniques in Gastrointestinal Endoscopy* 2006, 8, 33-37; d) J. Tambiah, R. Rawlins, D. Robb, T. Treasure, *Interact Cardiovasc Thorac Surg* 2007, 6, 529-533; e) H. Zhang, L. P. Bre, T. Zhao, Y. Zheng, B. Newland, W. Wang, *Biomaterials* 2014, 35, 711-719; f) A. J. Singer, J. V. Quinn, R. E. Clark, J. E. Hollander, *Surgery* 2002, 131, 270-276; g) A. J. Singer, J. V. Quinn, J. E. Hollander, *Am J Emerg Med* 2008, 26, 490-496.
[7] a) Y. M. Bhat, S. Banerjee, B. A. Barth, S. S. Chauhan, K. T. Gottlieb, V. Konda, J. T. Maple, F. M. Murad, P. R. Pfau, D. K. Pleskow, U. D. Siddiqui, J. L. Tokar, A. Wang, S. A. Rodriguez, *Gastrointest Endosc* 2013, 78, 209-215; b) B. S. McDonald, D. A. Buckley, *Br J Dermatol* 2013; c) W. D. Spotnitz, S. Burks, *Transfusion* 2008, 48, 1502-1516; d) W. D. Spotnitz, S. Burks, *Clin Appl Thromb Hemost* 2010, 16, 497-514.
[8] a) N. Lang, M. J. Pereira, Y. Lee, I. Friehs, N. V. Vasilyev, E. N. Feins, K. Ablasser, E. D. O'Cearbhaill, C. Xu, A. Fabozzo, R. Padera, S. Wasserman, F. Freudenthal, L. S. Ferreira, R. Langer, J. M. Karp, P. J. Del Nido, *Sci Transl Med* 2014, 6, 218ra216; b) C. Li, T. Wang, L. Hu, Y. Wei, J. Liu, X. Mu, J. Nie, D. Yang, *Materials Science and Engineering: C* 2014, 35, 300-306; c) M. Mehdizadeh, H. Weng, D. Gyawali, L. Tang, J. Yang, *Biomaterials* 2012, 33, 7972-7983; d) W. Nie, X. Yuan, J. Zhao, Y. Zhou, H. Bao, *Carbohydrate Polymers* 2013, 96, 342-348; e) L. Ninan, *Biomaterials* 2003, 24, 4091-4099; f) S. Thirupathi Kumara Raja, T. Thiruselvi, G. Sailakshmi, S. Ganesh, A. Gnanamani, *Biochimica et Biophysica Acta (BBA)—General Subjects* 2013, 1830, 4030-4039; g) S. Y. Yang, E. D. O'Cearbhaill, G. C. Sisk, K. M. Park, W. K. Cho, M. Villiger, B. E. Bouma, B. Pomahac, J. M. Karp, *Nat Commun* 2013, 4, 1702; h) D. G. Barrett, G. G. Bushnell, P. B. Messersmith, *Adv Healthc Mater* 2013, 2, 745-755; i) G. Bilic, C. Brubaker, P. B. Messersmith, A. S. Mallik, T. M. Quinn, C. Haller, E. Done, L. Gucciardo, S. M. Zeisberger, R. Zimmermann, J. Deprest, A. H. Zisch, *Am J Obstet Gynecol* 2010, 202, 85 e81-89; j) C. E. Brubaker, H. Kissler, L. J. Wang, D. B. Kaufman, P. B. Messersmith, *Biomaterials* 2010, 31, 420-427; k) C. E. Brubaker, P. B. Messersmith, *Langmuir* 2012, 28, 2200-2205; l) C. M. Haller, W. Buerzle, A. Kivelio, M. Perrini, C. E. Brubaker, R. J. Gubeli, A. S. Mallik, W. Weber, P. B. Messersmith, E. Mazza, N. Ochsenbein-Koelble, R. Zimmermann, M. Ehrbar, *Acta Biomater* 2012, 8, 4365-4370; m) A. Kivelio, P. Dekoninck, M. Perrini, C. E. Brubaker, P. B. Messersmith, E. Mazza, J. Deprest, R. Zimmermann, M. Ehrbar, N. Ochsenbein-Koelble, *Eur J Obstet Gynecol Reprod Biol* 2013, 171, 240-245; n) B. P. Lee, P. B. Messersmith, J. N. Israelachvili, J. H. Waite, *Annu Rev Mater Res* 2011, 41, 99-132; o) H. Lee, B. P. Lee, P. B. Messersmith, *Nature* 2007, 448, 338-341; p) A. Mandavi, L. Ferreira, C. Sundback, J. W. Nichol, E. P. Chan, D. J. Carter, C. J. Bettinger, S. Patanavanich, L. Chignozha, L. Ben-Joseph, A. Galakatos, H. Pryor, I. Pomerantseva, P. T. Masiakos, W. Faquin, A. Zumbuehl, S. Hong, J. Borenstein, J. Vacanti, R. Langer, J. M. Karp, *Proc Natl Acad Sci USA* 2008, 105, 2307-2312.
[9] S. Rose, A. Prevoteau, P. Elziere, D. Hourdet, A. Marcellan, L. Leibler, *Nature* 2014, 505, 382-385.
[10] a) M. Levy, F. Lagarde, V. A. Maraloiu, M. G. Blanchin, F. Gendron, C. Wilhelm, F. Gazeau, *Nanotechnology* 2010, 21, 395103; b) M. Levy, N. Luciani, D. Alloyeau, D. Elgrabli, V. Deveaux, C. Pechoux, S. Chat, G. Wang, N. Vats, F. Gendron, C. Factor, S. Lotersztajn, A. Luciani, C. Wilhelm, F. Gazeau, *Biomaterials* 2011, 32, 3988-3999; c) M. Levy, C. Wilhelm, M. Devaud, P. Levitz, F. Gazeau, *Contrast Media Mol Imaging* 2012, 7, 373-383.
[11] a) E. Albéniz Arbizu, A. López San Román, M. Garcia González, J. R. Foruny Olcina, F. Garcia-Hoz Rosales, R. Bárcena Marugán, G. Plaza Palacios, L. A. Gil Grande, *Transplantation Proceedings* 2003, 35, 1911-1912; b) F. Berrevoet, B. de Hemptinne, *Dig Surg* 2007, 24, 288-293; c) M. T. de Boer, E. A. Boonstra, T. Lisman, R. J. Porte, *Dig Surg* 2012, 29, 54-61; d) H. Ding, J. Q. Yuan, J. H. Zhou, X. Y. Zheng, P. Ye, C. Mao, Q. Chen, *Curr Med Res Opin* 2013, 29, 387-394; e) D. Erdogan, O. R. Busch, D. J. Gouma, T. M. van Gulik, *Dig Surg* 2007, 24, 294-299; f) J. Gugenheim, L. C. Bredt, A. Iannelli, *Hepatogastroenterology* 2011, 58, 922-925; g) N. Katkhouda, *Ann Surg* 2008, 247, 399-400; author reply 400; h) W. Saad, D. Madoff, *Seminars in Interventional Radiology* 2012, 29, 071-080.
[12] J. D. Lloyd, M. J. Marque, 3rd, R. F. Kacprowicz, *Emerg Med Clin North Am* 2007, 25, 73-81.
[13] R. Agha, R. Ogawa, G. Pietramaggiori, D. P. Orgill, *J Surg Res* 2011, 171, 700-708.
[14] A. J. Singer, R. A. Clark, *N Engl J Med* 1999, 341, 738-746.
[15] M. Chaouat, C. Le Visage, W. Baille, B. Escoubet, F. Chaubet, M. Mateescu, D. Letourneur, *Adv. Funct. Mater.* 2008, 18, 1-3.
[16] C. Le Visage, O. Gournay, N. Benguirat, S. Hamidi, L. Chaussumier, N. Mougenot, J. A. Flanders, R. Isnard, J. B. Michel, S. Hatem, D. Letourneur, F. Norol, *Tissue Eng Part A* 2012, 18, 35-44.
[17] W. Stöber W., A. Fink, E. Bohn, *J. colloid Interface Sci.* 1968, 26, 62-69.

The invention claimed is:
1. A method for adhering a biological tissue surface to a second surface in a subject in need thereof comprising the steps of administering nanoparticles in the form of an aqueous suspension to at least one of the biological tissue surface and the second surface and bringing the biological tissue surface and the second surface into contact for a time sufficient for the biological tissue surface and the second surface to adhere to each other, wherein the second surface is a hydrogel scaffold, wherein the nanoparticles are silica nanoparticles or iron oxide nanoparticles, and wherein the aqueous suspension does not include a coagulation agent other than the nanoparticles.

2. The method of claim 1 wherein the biological tissue is selected from the group consisting of skin tissue, hair tissue, nail tissue, corneal tissue, tongue tissue, oral cavity tissue, esophageal tissue, anal tissue, urethral tissue, vaginal tissue, urinary epithelial tissue, salivary gland tissue, mammary gland tissue, lacrimal gland tissue, sweat gland tissue, prostate gland tissue, bulbourethral gland tissue, Bartholin's gland tissue, uterine tissue, respiratory and gastrointestinal tract goblet cell tissue, gastric mucosal tissue, gastric gland tissue, pancreatic tissue, spleen tissue, pulmonary tissue, pituitary gland tissue, thyroid gland tissue, parathyroid gland tissue, testicular tissue, ovarian tissue, respiratory gland tissue, gastrointestinal gland tissue, adrenal gland tissue, renal tissue, liver tissue, adipose tissue, duct cell tissue, gall bladder tissue, epidydimal tissue, vas deferens tissue, blood vessel tissue, lymph gland tissue, lymphatic duct tissue, synovial tissue, serosal tissue, squamous tissue, cochlear tissue, choroid plexus tissue, ependymal tissue, dural tissue, pia-arachnoid tissue, sclera tissue, retinal tissue, iris tissue, ciliary tissue, dental tissue, otic tissue, ligament tissue, tendon tissue, elastic cartilage tissue, fibrocartilage tissue, hyaline cartilage tissue, bone marrow tissue, intervertebral disc tissue, compact bone tissue, cancellous bone tissue, skeletal muscle tissue, cardiac muscle tissue, smooth muscle tissue, cardiac valve tissue, pericardial tissue, pleural tissue, peritoneal tissue, blood cell tissue, neuronal tissue, glial tissue, sensory transducer cell tissue, pain sensitive tissue, autonomic neuron tissue, peripheral nervous system tissue, cranial nerve tissue, ocular lens tissue, germ cell tissue, thymus tissue, placental tissue, fetal membrane tissue, umbilical tissue, stem cell tissue, mesodermal tissue, ectodermal tissue, endodermal tissue, autologous tissue, and allograft tissue or a combination thereof.

3. The method of claim 1, wherein the hydrogel scaffold further comprises a biologically active agent, a pharmaceutical agent or a radiosensitizer.

4. The method of claim 1 wherein the hydrogel scaffold is loaded with a plurality of cells.

5. The method according claim 1, wherein the nanoparticles are detectable by an imaging technique selected from the group consisting of ultrasonography, elastography, Supersonic Shear Wave Imaging, Magnetic Resonance Imaging (MRI), Positron Emission Tomography (PET), Single Photon Emission Computed Tomography (SPECT), fluorescence spectroscopy, Computed Tomography, and X-ray radiography, or by a combination of these techniques.

6. The method according to claim 1, wherein a solvent in the aqueous suspension is an organic solvent.

7. The method according to claim 1, wherein the nanoparticles are administered with a technique selected from the group consisting of coating, dipping, spraying, spreading and solvent casting.

8. The method according to claim 1, (i) wherein the silica or iron oxide nanoparticles are administered in the form of the aqueous suspension to the biological tissue surface; and (ii) further comprising adsorbing additional silica or iron oxide nanoparticles to the second surface, prior to bringing the biological tissue surface and the second surface into contact.

9. The method according to claim 1, wherein (i) the silica or iron oxide nanoparticles are administered in the form of the aqueous suspension to the biological tissue surface, and (ii) the second surface comprises additional silica or iron oxide nanoparticles adsorbed thereon.

10. The method according to claim 1, wherein one or both of said nanoparticles and said second surface includes a drug to control bleeding, treat infection or malignancy, or promote tissue regeneration.

11. The method according to claim 1, wherein the aqueous suspension consists essentially of a solvent and nanoparticles.

12. A method of controlling bleeding at a biological tissue surface by adhering the biological tissue surface to a second surface, comprising administering nanoparticles in the form of an aqueous suspension to at least one of the biological tissue surface and the second surface and bringing the biological tissue surface and the second surface into contact for a time sufficient for the biological tissue surface and the second surface to adhere to each other, wherein the second surface is a hydrogel scaffold, wherein the nanoparticles are silica nanoparticles or iron oxide nanoparticles, and wherein the aqueous suspension does not include a coagulation agent other than the nanoparticles.

13. A method for sealing a defect between a first biological tissue and a second biological tissue by adhering a surface of the first biological tissue to a surface of the second biological tissue, comprising:

administering nanoparticles in the form of an aqueous suspension to at least one of the first biological tissue surface and the second biological tissue surface; and bringing the first biological tissue surface and the second biological tissue surface into contact for a time sufficient for the first biological tissue surface and the second biological tissue surface to adhere to each other; and wherein the nanoparticles are silica nanoparticles or iron oxide nanoparticles; and wherein the aqueous suspension does not include a coagulation agent other than the nanoparticles.

14. The method of claim 13, wherein the first biological tissue surface and the second biological tissue surface are brought into contact by sutures, staples, mechanical fixators, or mesh.

15. A method of performing tissue engineering by adhering a biological tissue surface to a second surface, comprising administering nanoparticles in the form of an aqueous suspension to at least one of the biological tissue surface and the second surface and bringing the biological tissue surface and the second surface into contact for a time sufficient for the biological tissue surface and the second surface to adhere to each other, wherein the second surface is a hydrogel scaffold, wherein the nanoparticles are silica nanoparticles or iron oxide nanoparticles, and wherein the aqueous suspension does not include a coagulation agent other than the nanoparticles.

16. A method for building an assembly made with a multilayer of biological tissues and materials comprising
   i) administering nanoparticles in the form of an aqueous suspension to one or both of a surface of a biological tissue layer and a surface of a material layer, and
   ii) bringing the surface of the biological tissue layer and the surface of the material layer into contact for a time sufficient for the surface of the biological tissue layer and the surface of the material layer to adhere to each other, and
   iii) repeating steps i) and ii) a plurality of times to form the multilayer of biological tissues and materials,
   wherein each material layer is a hydrogel scaffold,
   wherein the nanoparticles are silica nanoparticles or iron oxide nanoparticles, and
   wherein the aqueous suspension does not include a coagulation agent other than the nanoparticles.

17. A method of performing surgery that requires adhering a biological tissue surface to a second surface in a subject in need thereof, comprising the steps of
   administering nanoparticles in the form of an aqueous suspension to at least one of the biological tissue surface and the second surface and
   bringing the biological tissue surface and the second surface into contact for a time sufficient for the biological tissue surface and the second surface to adhere to each other,
   wherein the second surface is a hydrogel scaffold,
   wherein the nanoparticles are silica nanoparticles or iron oxide nanoparticles, and
   wherein the aqueous suspension does not include a coagulation agent other than the nanoparticles.

18. The method according to claim 17, wherein the surgery is selected from the group consisting of bariatric surgery, cardiac surgery, thoracic surgery, colon and rectal surgery, dermatologic surgery, general surgery, gynecologic surgery, maxillofacial surgery, neurosurgery, obstetric surgery, oncologic surgery, ophthalmologic surgery, oral surgery, orthopedic surgery, otolaryngologic surgery, pediatric surgery, plastic surgery, cosmetic and reconstructive surgery, podiatric surgery, spine surgery, transplant surgery, trauma surgery, vascular surgery, urologic surgery, dental surgery, veterinary surgery, endoscopic surgery, anesthesiology, an interventional radiologic procedure, an emergency medicine procedure, a battlefield procedure, a deep or superficial laceration repair, a cardiologic procedure, an internal medicine procedure, an intensive care procedure, an endocrinologic procedure, a gastroenterologic procedure, a hematologic procedure, a hepatologic procedure, a diagnostic radiologic procedure, an infectious disease procedure, a nephrologic procedure, an oncologic procedure, a proctologic procedure, a pulmonary medicine procedure, a rheumatologic procedure, a pediatric procedure, a physical medicine or rehabilitation medicine procedure, a geriatric procedure, a palliative care procedure, a medical genetic procedure, and a fetal procedure, or a combination thereof.

* * * * *